United States Patent
Spira et al.

(10) Patent No.: US 10,322,182 B2
(45) Date of Patent: *Jun. 18, 2019

(54) LYOPHILIZED PREPARATION OF CYTOTOXIC DIPEPTIDES

(71) Applicant: ONCOPEPTIDES AB, Stockholm (SE)

(72) Inventors: Jack Spira, Tyresö (SE); Fredrik Lehmann, Knivsta (SE)

(73) Assignee: ONCOPEPTIDES AB, Stockholm (SE)

( * ) Notice: Subject to any disclaimer, the term of this patent is extended or adjusted under 35 U.S.C. 154(b) by 0 days.

This patent is subject to a terminal disclaimer.

(21) Appl. No.: 15/225,323

(22) Filed: Aug. 1, 2016

(65) Prior Publication Data

US 2017/0049894 A1    Feb. 23, 2017

Related U.S. Application Data

(63) Continuation of application No. 14/113,768, filed as application No. PCT/EP2012/057577 on Apr. 25, 2012.

(60) Provisional application No. 61/535,126, filed on Sep. 15, 2011.

(30) Foreign Application Priority Data

Apr. 28, 2011 (SE) ................................. 1150371

(51) Int. Cl.
```
A61K 38/00      (2006.01)
A61K 47/10      (2017.01)
A61K 47/26      (2006.01)
A61K 47/40      (2006.01)
A61K 9/19       (2006.01)
A61K 31/195     (2006.01)
A61K 38/05      (2006.01)
A61K 47/12      (2006.01)
F26B 5/06       (2006.01)
A61K 31/222     (2006.01)
A61K 47/02      (2006.01)
```

(52) U.S. Cl.
CPC ............... *A61K 47/10* (2013.01); *A61K 9/19* (2013.01); *A61K 31/195* (2013.01); *A61K 31/222* (2013.01); *A61K 38/00* (2013.01); *A61K 38/05* (2013.01); *A61K 47/02* (2013.01); *A61K 47/12* (2013.01); *A61K 47/26* (2013.01); *A61K 47/40* (2013.01); *F26B 5/06* (2013.01)

(58) Field of Classification Search
None
See application file for complete search history.

(56) References Cited

U.S. PATENT DOCUMENTS

| | | | |
|---|---|---|---|
| 4,997,651 | A | 3/1991 | Poole et al. |
| 7,754,720 | B2 | 7/2010 | Bondy et al. |
| 2004/0034099 | A1 | 2/2004 | Ramsey |
| 2004/0097421 | A1* | 5/2004 | Lewensohn .......... C07K 5/0827 560/41 |
| 2014/0038996 | A1* | 2/2014 | Inghelbrecht ............ A61K 9/19 514/275 |
| 2014/0128462 | A1 | 5/2014 | Spira et al. |
| 2015/0335578 | A1 | 11/2015 | Spira et al. |
| 2016/0271065 | A1 | 9/2016 | Spira et al. |

FOREIGN PATENT DOCUMENTS

| | | |
|---|---|---|
| CN | 101584669 A | 11/2009 |
| EP | 2 599 484 A1 | 6/2013 |
| JP | H01153628 A | 6/1989 |
| JP | 2004503564 A | 2/2004 |
| JP | 2005526771 A | 9/2005 |
| JP | 2007504267 A | 3/2007 |
| JP | 2008525362 A | 7/2008 |
| JP | 2009513618 A | 4/2009 |
| WO | 01/96367 | 12/2001 |
| WO | 03/077882 | 9/2003 |
| WO | 2004/103274 | 12/2004 |
| WO | 2005/025499 | 3/2005 |
| WO | 2006/066949 | 6/2006 |
| WO | 2007/052076 | 5/2007 |
| WO | 2011/078782 | 6/2011 |
| WO | 2014/065751 | 5/2014 |

OTHER PUBLICATIONS

Baheti, A., et al, Excipients used in lyophilization of small molecules, J. Excipients and Food Chem. 1 (1) 2010, p. 41-54.*
Bedu-Addo, Understanding Lyophilization Formulation Development, Pharmaceutical Technology Lyopilization 2004, p. 10-18.*
Melphalan flufenamide | CAS#380449514 | alkylating agent | MedKoo (2017) 5 pages.*
Melphalan DrugBank 2/272017 11 pages.*
Pilaniya, K., Recent trends in the impurity profile of pharmaceuticals, J Adv Pharm Technol Res. Jul.-Sep. 2010; 1(3): 302-310.*
Hughes, JP., et al., Principles of Early Drug Discovery, British Journal of Pharmacology (2011) 162 1239-1249.*
Zezhao Hua, ed., 2005, "Protective agents and additives for freeze drying," pp. 198-199 of Chapter 8 in *New Technology of Freeze Drying*, Science Press, Beijing (with English translation).
Allison et al., 1999, "Hydrogen Bonding between Sugar and Protein Is Responsible for Inhibition of Dehydration-Induced Protein Unfolding," Archives of Biochemistry and Biophysics 365(2):289-98.

(Continued)

*Primary Examiner* — Thomas S Heard
(74) *Attorney, Agent, or Firm* — Biospark Intellectual Property Law

(57) ABSTRACT

The present invention is directed to novel lyophilized pharmaceutical preparations comprising a cytotoxic dipeptides such as melphalan flufenamide and one or more excipient(s) selected from the group comprising a polysorbate; a polyethylene glycol; β-cyclodextrin; ocyclodextrin; hydroxypropyl-β-cyclodextrin; sulfobutylether-β-cyclodextrin; lactose; benzyl alcohol; disodium succinate; propylene glycol; Cremophor EL; Dimethyl sulfoxide; D-mannitol; Trehalose; Sucrose and an amino acid. This preparation may be further formulated and is useful in cancer therapy.

16 Claims, 21 Drawing Sheets

(56) References Cited

OTHER PUBLICATIONS

Arshinova et al., 2013, "Adjuvant substances in the freeze-drying technology of medicaments," Scientific and Production Magazine 1(2):20-24 (with English translation).
Barley, "Basic Principles of Freeze Drying," https://www.spscientific.com/freeze-drying-lyophilization-basics/ downloaded on Mar. 13, 2018.
Hughes, 2011, "Principles of Early Drug Discovery," British Journal of Pharmacology 162: 1239-1249.
Ingvarsson et al., 2011, "Stabilization of liposomes during drying," Expert Opin. Drug Deliv. 8(3): 375-388.
Kasraian and DeLuca, 1995, "The Effect of Tertiary Butyl Alcohol on the Resistance of the Dry Product Layer During Primary Drying," Pharmaceutical Research 12(4): 491-495.
Lomas et al. 1997, "Commercial plasma $\alpha_1$-antitrypsin (Prolastin®) contains a conformationally inactive, latent component," Eur Respir J. 10: 672-675.
Rowe et al., 2006, "Sucrose," in *Handbook of Pharmaceutical Excipients*, fifth ed., pp. 744-747.
Yu et al., 2005, "Freeze drying (lyophilization) of genetic engineering pharmaceuticals," Chinese Journal of Bioprocess Engineering 5:58-63 (with English translation).
Zezhao Hua, 2005, "Freeze-drying Protectants and Additives," pp. 179-213 of Chapter 8 in *Novel Freeze-Drying Technologies*, Science Press, Beijing (entire chapter with English translation).
p. 3-251 from the FDA's Orange Book.
Alkeran product insert.
Gullbo et al., 2003, "Structure-Activity Relationship for Alkylating Dipeptide Nitrogen Mustard Derivatives," Oncology Research 14:113-132.
Nehate et al., 2014, "Paclitaxel Formulations: Challenges and Novel Delivery Options," Curr. Drug Deliv. 11(6):666-86.
Ambisome® product insert.
Fu et al., eds., 2008, "Auxiliary Materials in lyophilized preparations," Chapter 11 in *The Science of Auxiliary Materials in Pharmaceutics*, Press of Chinese Traditional Medicine (including English translation).
International Preliminary Report on Patentability, issued in PCT/SE2013/051246, dated Feb. 9, 2015.
International Search Report, issued in PCT/SE2013/051246, dated Feb. 7, 2014.
Nema et al., 1997, "Excipients and Their Use in Injectable Products," PDA Journal of Pharmaceutical Science & Technology 51(4):166-171.
First Office Action dated Mar. 1, 2016 in connection with Japanese Patent Application No. 2014-506850 (including English translation).
Decision of Patent dated Oct. 11, 2016 in connection with Japanese Patent Application No. 2014-506850 (including English translation).
International Preliminary Report on Patentability and Written Opinion of the International Searching Authority (Forms PCT/IB/326, PCT/IB/373 and PCT/ISA/237), dated Nov. 7, 2013, for corresponding International Application No. PCT/EP2012/057577.
International Search Report issued in PCT/EP2012/057577, dated Jun. 5, 2012.
Baheti, et al., 2010, "Excipients used in lyophilization of small molecules," Journal of Excipients and Food Chemicals, 1(1):41-54.
Wickstrom, M., 2007, "Preclinical Studies of the Melphalan Prodrug J1 for Cancer Therapy," ACTA Universitatis Upsaliensis UPPSALA.

\* cited by examiner

LYOPHILIZED PREPARATION OF CYTOTOXIC DIPEPTIDES

This application is a continuation of U.S. application Ser. No. 14/113,768, which is a national stage application of international application no. PCT/EP2012/057577, filed Apr. 25, 2012, which claims the priority benefit of U.S. provisional application No. 61/535,126, filed Sep. 15, 2011, and Swedish application no. 1150371-1, filed Apr. 28, 2011, the contents of each of which are incorporated by reference herein in their entireties.

TECHNICAL FIELD

The present invention is directed to lyophilized pharmaceutical preparations comprising cytotoxic dipeptides or pharmaceutically acceptable salts thereof, methods for their preparation, compositions comprising the lyophilized pharmaceutical preparations and their use in the treatment of cancer.

BACKGROUND ART

Cancer is a disease which is difficult to cure and which may be fatal. Accordingly, efforts to develop new therapies for cancer are constantly ongoing in the research society. The vast majorities of cancers are present as solid tumors, e.g. lung cancer, breast cancer, prostate cancer, while the rest are hematological and lymphoid malignancies, e.g. leukemias and lymphomas.

Chemotherapy is often used in attempts to cure or palliate the disease. As cancer cells typically divide rapidly, chemotherapy usually acts by killing rapidly dividing cells. In the broad sense, most chemotherapeutic drugs work by impairing mitosis (i.e. cell division), effectively targeting fast-dividing cells. As these drugs cause damage to cells they are termed cytotoxic. Some drugs cause cells to undergo apoptosis (so-called "programmed cell death"). Often combination chemotherapy is used, when two or more drugs having different modes of action are used together in order to optimise the antitumoral effect, to minimise side effects, and prevent resistance development. The results obtained with chemotherapy vary according to tumor type. Some tumors are very sensitive and the treatment has then a high probability of leading to cure.

Chemotherapeutic drugs can generally be divided into alkylating agents, antimetabolites, anthracyclines, plant alkaloids, topoisomerase inhibitors, and other antitumor agents. The drugs affect cell division or DNA synthesis.

Alkylating agents, such as drugs derived from nitrogen mustard, that is bis(2-chloroethyl)amine derivatives, are used as chemotherapeutic drugs in the treatment of a wide variety of neoplastic diseases. Alkylating agents have the ability to covalently attach alkyl groups to electronegative sites in cells. Thus, these agents act by impairing cell function by forming covalent bonds with heteroatoms in biologically important molecules like RNA, DNA and proteins. Examples of alkylating agents are mechlorethamine, cyclophosphamide, chlorambucil, ifosfamide, temozolomide and melphalan that chemically modify a cell's DNA.

WO01/96367 discloses alkylating di- and tripeptides and one or two additional amino acids or amino acid derivatives. These derivatives were demonstrated to have an improved efficacy on a variety of tumor types.

Melphalan, i.e. p-[bis-(2-chloroethyl)amino]phenylalanine, is a conjugate of nitrogen mustard and the amino acid phenylalanine, which was synthesised in the mid 1950s (U.S. Pat. No. 3,032,584). This classic alkylating substance soon became a valuable drug in the chemotherapeutic field and is still of importance in the treatment of for example myeloma. Clinical use of melphalan in the treatment of late stage solid tumors has, however, had limited efficacy. In the search for a more selective action on malignant cells melphalan analogues have therefore been synthesised.

Larionov L. F., Cancer Res (1961), 21, 99-104 discloses various melphalan-related derivatives.

STN registry files RN: 1060633-95-5, RN: 887609-28-1, RN 790650-89-4, RN: 781606-39-1, RN: 773046-98-3, RN: 767621-58-9, RN: 760165-58-0 and RN: 757941-61-0 discloses various melphalan-related derivatives.

Koltun, M et al., Biopharmaceutics & Drug disposition (210), 31, 450-454 discloses forms of melphalan.

Ma D Q et al., International Journal of Pharmaceutics (1999), 189, 227-234 discloses discloses forms of melphalan.

Murav'ev I et al., Farmatsiya (1978), 27, (2), 13-15 (with abstract in Chemical Abstracts no. 1978:412066) discloses melphalan-related derivatives.

Lyophilization or freeze-drying is a method for dehydrating samples used to preserve or increase stability or to stop degradation. Due to the low water content of lyophilized products, typically around 1-4%, the action of microorganisms and enzymes is inhibited and the product life thereby increased. In lyophilization, the sample to be lyophilized is dissolved in an aqueous solution and subsequently frozen after which the surrounding pressure is reduced. The sample is then submitted to sublimation, optionally by the application of heat, in order to sublime the frozen water directly from the solid phase to the gas phase. The final water content in the product is very low, typically around 1% to 4%. Lyophilization is commonly used in the pharmaceutical field in order to increase the shelf life of pharmaceutical products.

SUMMARY OF THE INVENTION

In general, lipophilic dipeptide ester derivatives suffer from a poor solubility in aqueous solutions. Therefore, the use of organic solvents, such as DMA (dimethylacetamide), is necessary in order to dissolve such dipeptides. However, organic solvents are often toxic and may also cause destruction of medical devices used for the administration of the dipeptides to subjects, such as cancer patients. Consequently, to overcome the problems with dissolving and providing the cytotoxic dipeptides in an organic solvent, there is a need for alternative pharmaceutical preparations of cytotoxic dipeptides having sufficient solubility in physiologically acceptable solutions.

The present invention refers to lyophilized preparations comprising melphalanyl-L-p-fluorophenylalanine ethyl ester, also known as melphalan flufenamide, as well as pharmaceutically acceptable salt thereof, in particularly, melphalanyl-L-p-fluorophenylalanine ethyl ester hydrochloride, also known as melphalan flufenamide hydrochloride, or J1.

An aspect of the present invention is directed to a lyophilized pharmaceutical preparation comprising
(i) melphalan flufenamide, or a pharmaceutically acceptable salt thereof; and
(ii) at least one excipient selected from the group comprising
a polysorbate; a polyethylene glycol; β-cyclodextrin; α-cyclodextrin; hydroxypropyl-β-cyclodextrin; sulfobutylether-β-cyclodextrin; lactose; benzyl alcohol;

disodium succinate; propylene glycol; Cremophor EL; Dimethyl sulfoxide; D-mannitol; Trehalose; Sucrose and an amino acid.

Still an aspect of the present invention is a lyophilized pharmaceutical preparation which is soluble in an aqueous solution.

Yet an aspect of the present invention is a method for the preparation of a lyophilized pharmaceutical preparation as herein described, whereby:
  a. melphalan flufenamide, or a pharmaceutically acceptable salt thereof, is dissolved in an organic solvent to obtain a melphalan flufenamide solution;
  b. water is added to the melphalan flufenamide solution in order to obtain an aqueous melphalan flufenamide solution, in a concentration of about 0.2-3.0 mg/ml;
  c. at least one excipient selected from the group comprising a polysorbate;
     a polyethylene glycol; β-cyclodextrin; α-cyclodextrin; hydroxypropyl-β-cyclodextrin; sulfobutylether-β-cyclodextrin; lactose; benzyl alcohol; disodium succinate; propylene glycol; Cremophor EL; Dimethyl sulfoxide; D-mannitol; Trehalose; Sucrose and an amino acid is added to the melphalan flufenamide solution; and
  d. the aqueous melphalan flufenamide solution containing excipient(s) is subjected to lyophilization.

Still an aspect of the invention is a kit of parts, comprising a first container comprising a lyophilized pharmaceutical preparation as defined herein, and a second container comprising a physiologically acceptable solution.

Still an aspect of the present invention is a lyophilized pharmaceutical preparation as herein described, for use as a medicament.

Yet an aspect of the invention is a kit of parts as herein described, for use as a medicament.

An aspect of the present invention is a lyophilized pharmaceutical preparation as herein described, for use in the treatment and/or prevention of cancer, such as ovarian cancer, lung cancer, bladder cancer, mesothelioma, multiple myeloma, breast cancer, and/or any solid or hematological cancer.

Yet an aspect of the invention is a kit of parts as herein described, for use in the treatment and/or prevention of cancer, such as ovarian cancer, lung cancer, bladder cancer, mesothelioma, multiple myeloma, breast cancer, and/or any solid or hematological cancer.

Still an aspect of the invention is a method for the treatment of and/or prevention of cancer, such as ovarian cancer, lung cancer, bladder cancer, mesothelioma, multiple myeloma, breast cancer, and/or any solid or hematological cancer, whereby a lyophilized pharmaceutical preparation as described herein, is administered in a therapeutically effective dose to a subject in need thereof.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will supercede. In addition, the materials, methods, and examples are illustrative only and not intended to be limiting.

Other features and advantages of the invention will be apparent from the following detailed description, drawings, examples, and from the claims.

DETAILED DESCRIPTION OF THE INVENTION

Figure 1A:
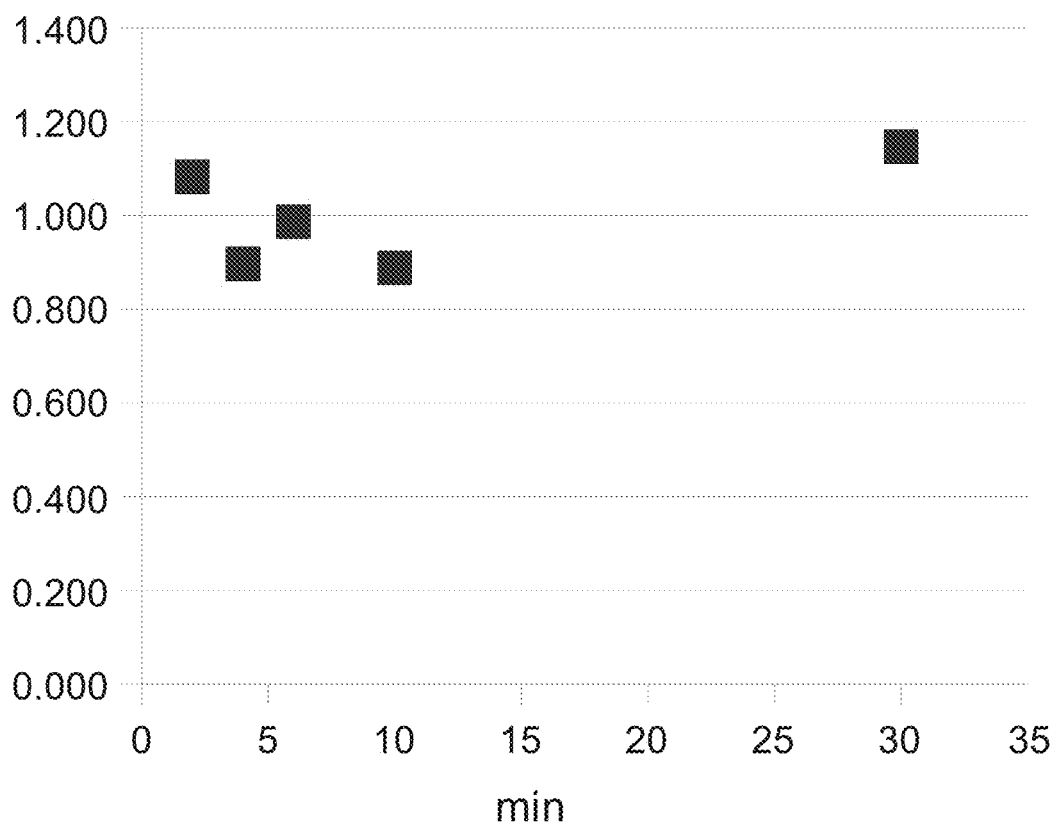
FIGS. 1A-D contain graphs of four repeated dissolution speed measurements of melphalan flufenamide lyophilized without excipients by method A according to Example 2. Samples were withdrawn at the indicated time points and the amount of dissolved melphalan flufenamide was determined by HPLC. The y-axis shows the amount of melphalan flufenamide in mg/ml.
Figure 1B:
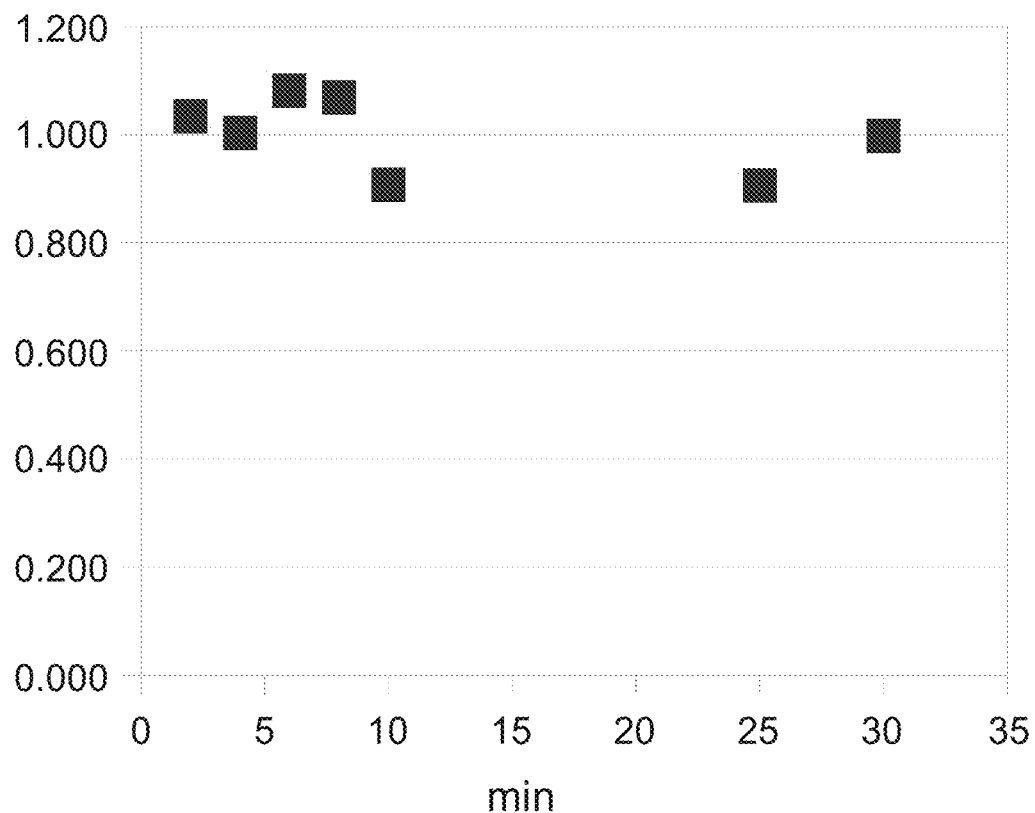
Figure 1C:
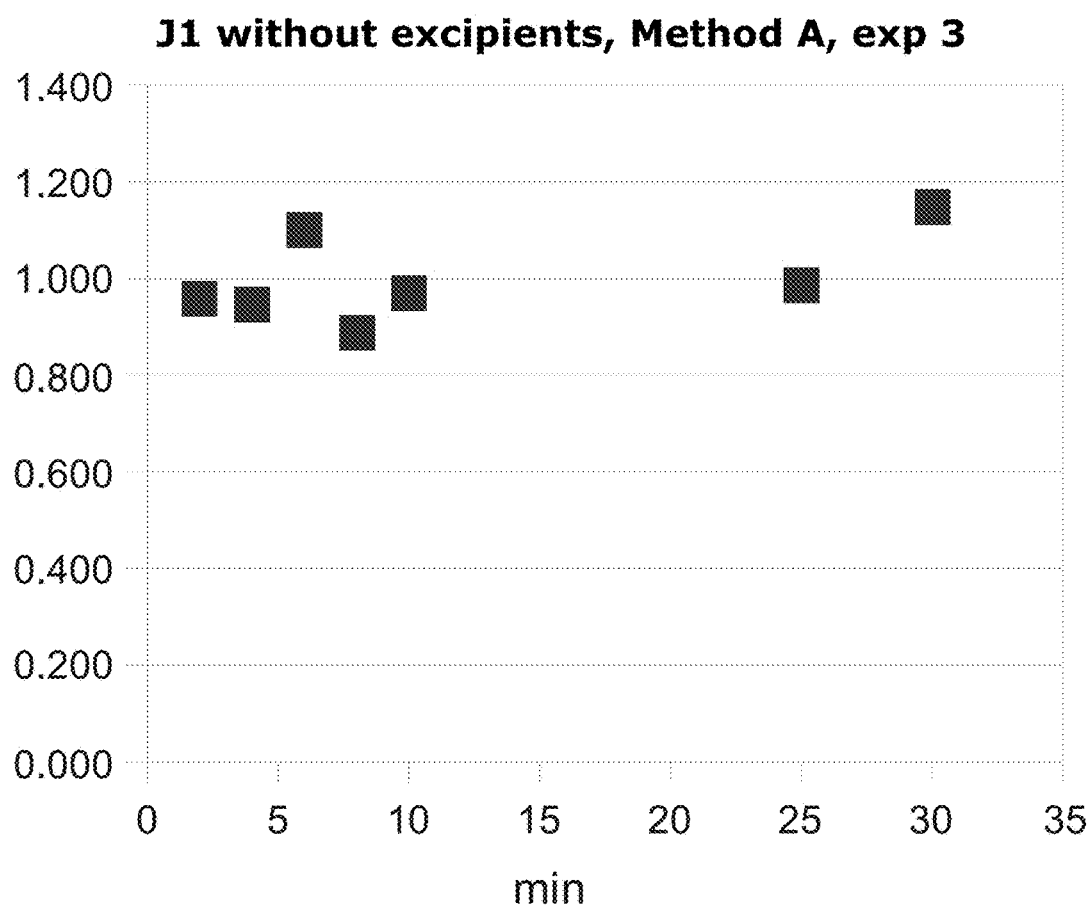
Figure 1D:
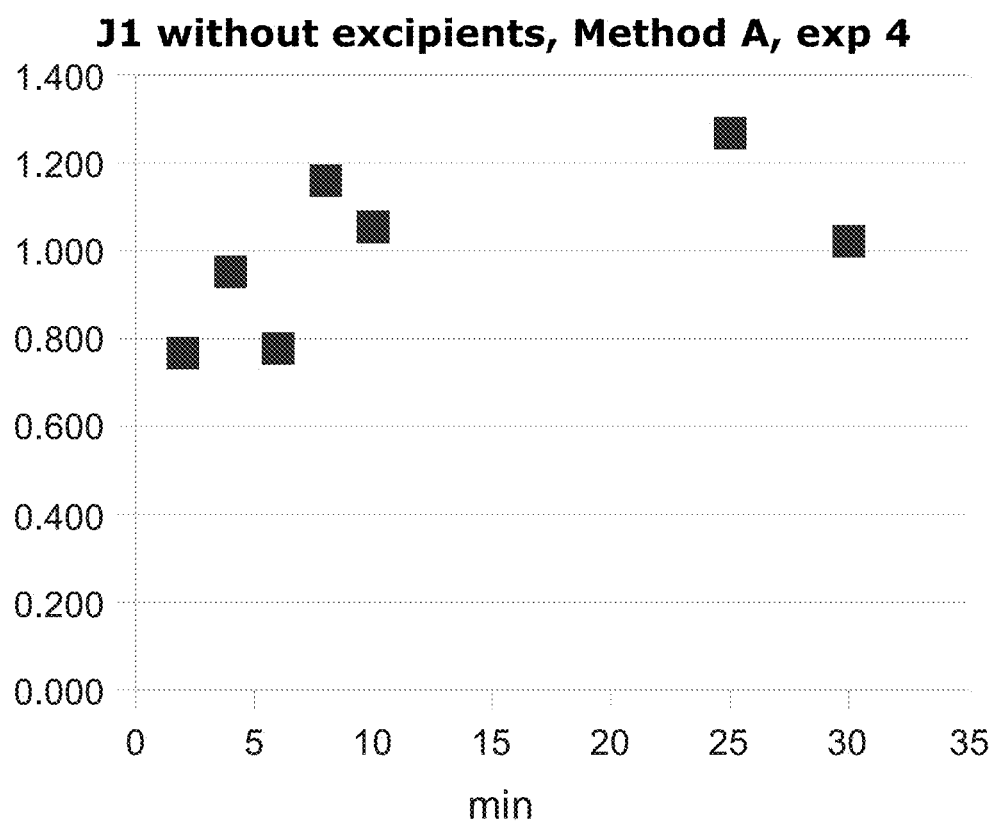
Figure 2A:
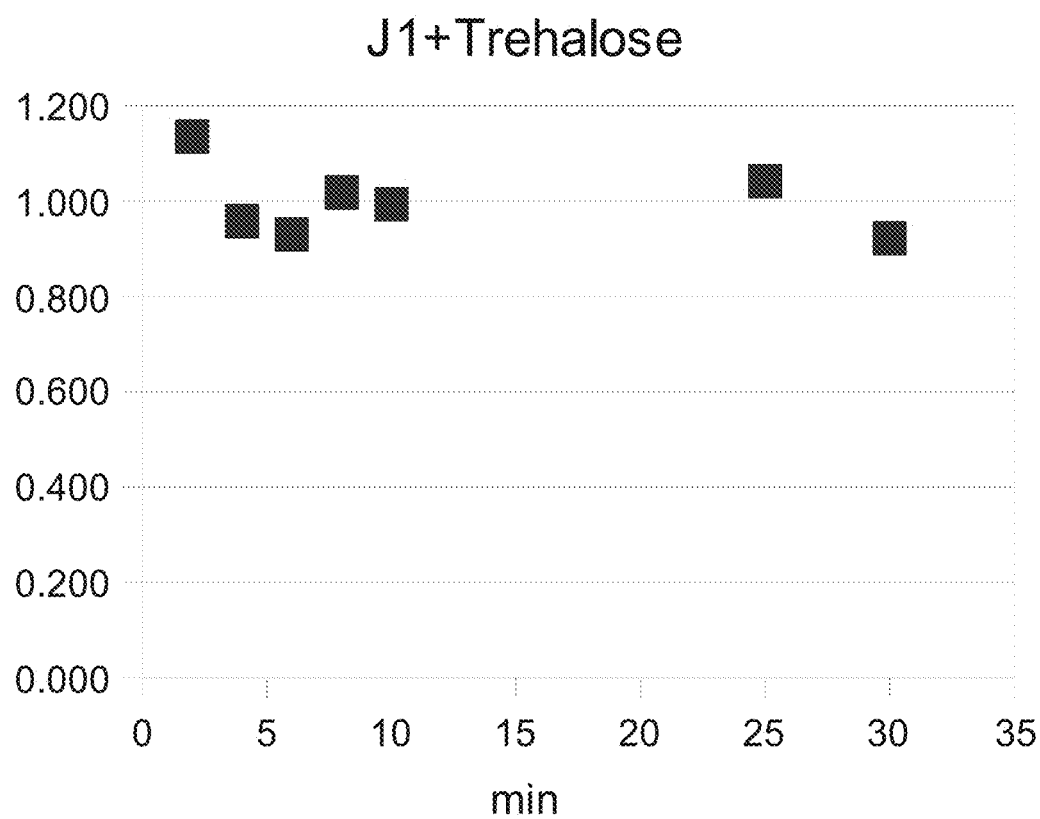
FIGS. 2A-E contain graphs of dissolution speed measurements of melphalan flufenamide lyophilized in the presence of excipients as indicated in the figures by method A according to Example 2. Samples were withdrawn at the indicated time points and the amount of dissolved melphalan flufenamide was determined by HPLC. The y-axis shows the amount of melphalan flufenamide in mg/ml.
Figure 2B:
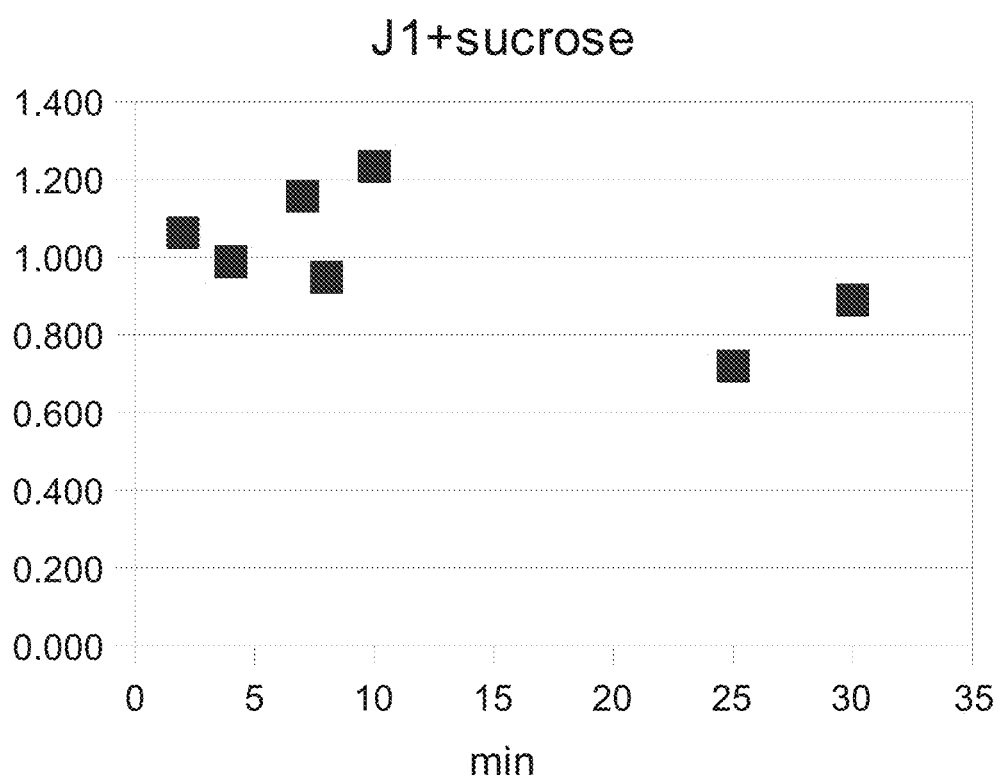
Figure 2C:
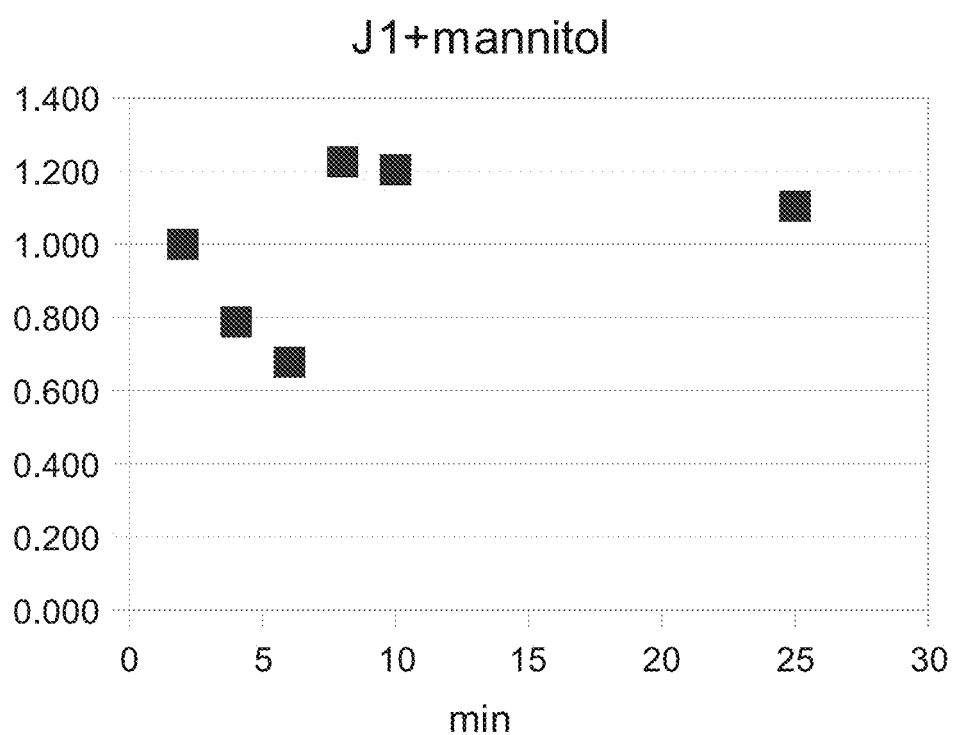
Figure 2D:
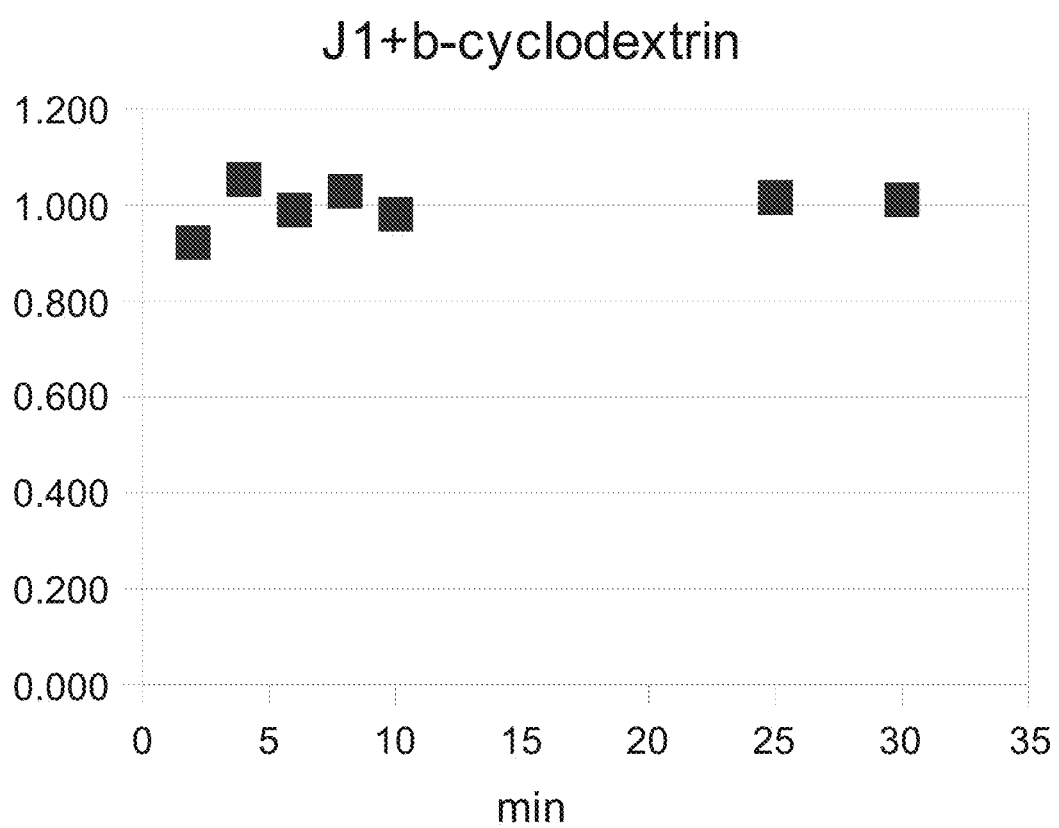
Figure 2E:
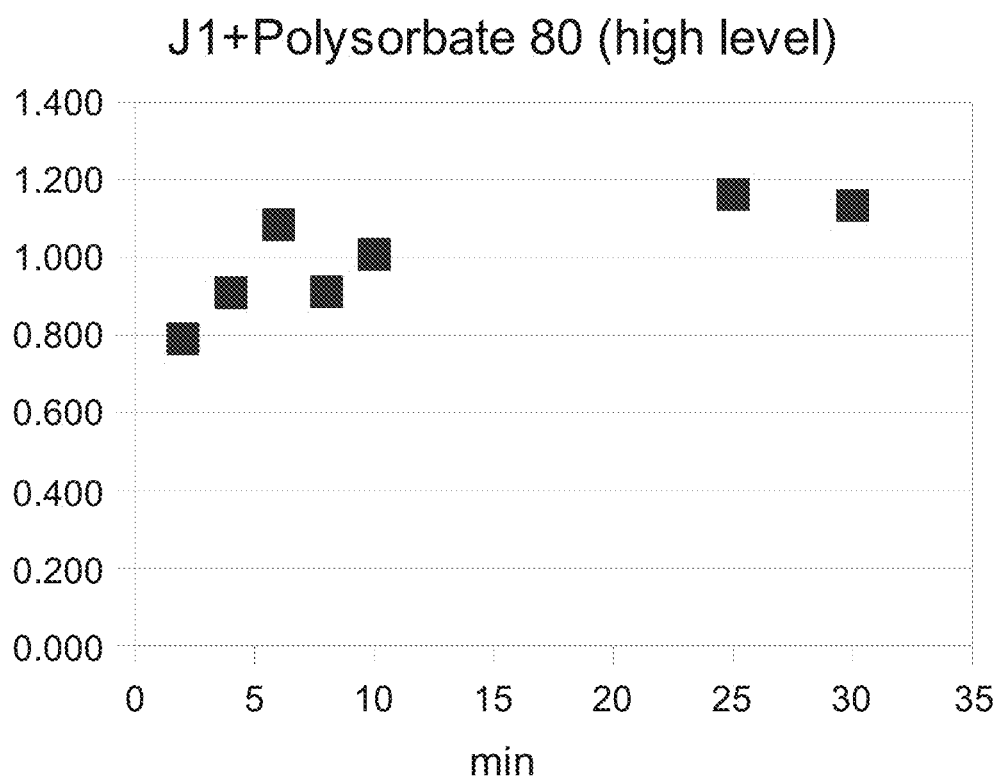

Non-lyophilized cytotoxic dipeptides or pharmaceutically acceptable salts thereof may have a low solubility in aqueous solutions, which may necessitate the use of organic solvents, such as DMA (dimethylacetamide), for dissolving said dipeptides or pharmaceutically acceptable salts thereof. Therefore, when a cytotoxic dipeptide is to be administered to a patient, the substance first has to be dissolved in an organic solvent, such as DMA, and thereafter diluted in a solution for infusion before administration to the patient. The patient is by this method exposed to organic solvents, the exposure of which may be hazardous for the patient. Also, the organic solvent may destroy the medical devices used for the administration of melphalan flufenamide to subjects, such as cancer patients.

The present inventors have now surprisingly found that when certain cytotoxic dipiptides or pharmaceutically acceptable salts thereof are lyophilized in the presence of an excipient, the resulting lyophilized pharmaceutical preparation can have an even higher solubility in a physiologically acceptable solution. In fact, the solubility can be so high that the step of dissolving the cytotoxic dipeptide or pharmaceutically acceptable salt thereof in an organic solvent can be omitted and the cytotoxic dipeptide can be directly dissolved in an aqueous, physiologically acceptable solution and administered to a patient. Preferably, said cytotoxic dipeptide is melphalan flufenamide or a pharmaceutically acceptable salt thereof.

In previous preparations, melphalan flufenamide was obtained from synthesis as a white powder in crystalline form. This crystalline form can only be dissolved in highly acidic aqueous solutions, which for practical manufacturing purposes is impossible. The presence of excipients as such, did not sufficiently improve the solubility. Therefore, previously melphalan flufenamide was instead dissolved in DMA (dimethylacetamide) in a glucose solution. The preparation is feasible but is unstable: 7% degradation/h. Furthermore, dimerization occurs and the solution turns bright yellow. This preparation was, however, unreliable and the polymerization rate varied in an unacceptable manner.

Consequently, there is a need for identifying alternative ways of providing a preparation comprising melphalan flufenamide or a pharmaceutically acceptable salt thereof that is soluble with increased stability. Further, the preparation should be water-soluble to avoid negative issues of having an organic solvent in the product that is provided to the patient (such as DMA).

An aspect of the present invention is a lyophilized pharmaceutical preparation comprising
(i) melphalan flufenamide, or a pharmaceutically acceptable salt thereof; and
(ii) at least one excipient selected from the group comprising a polysorbate; a polyethylene glycol; β-cyclodextrin; α-cyclodextrin; hydroxypropyl-β-cyclodextrin; sulfobutylether-β-cyclodextrin; lactose; benzyl alcohol; disodium succinate; propylene glycol; Cremophor EL; Dimethyl sulfoxide; D-mannitol; Trehalose; Sucrose; and an amino acid.

In one embodiment of this aspect, said excipient is selected from the group comprising Polysorbate 80; PEG 400; lactose; benzyl alcohol; disodium succinate; propylene glycol; PEG 300; Cremophor EL; Dimethyl sulfoxide; D-mannitol; Trehalose; Sucrose; and histidine.

In another embodiment of this aspect, said melphalan flufenamide is melphalan flufenamide hydrochloride (J1).

In another aspect of the invention, there is provided a pharmaceutical preparation comprising
(i) melphalan flufenamide hydrochloride (J1); and
(ii) at least one excipient selected from the group comprising a polysorbate; a polyethylene glycol; β-cyclodextrin; α-cyclodextrin; hydroxypropyl-β-cyclodextrin; sulfobutylether-β-cyclodextrin; lactose; benzyl alcohol; disodium succinate; propylene glycol; Cremophor EL; Dimethyl sulfoxide; D-mannitol; Trehalose; Sucrose; and an amino acid.

In one embodiment of this aspect, said at least one excipient is a polysorbate or polyethylene glycol.

In another embodiment of this aspect, said at least one excipient is Polysorbate 80.

In another embodiment of this aspect, said at least one excipient has surfactant properties. Such properties would increase the stability of the lyophilized pharmaceutical preparation. Said at least one excipient having surfactant properties may be polysorbate or polyethylene glycol, such as Polysorbate 80 or PEG400.

In another embodiment of this aspect the preparation comprises melphalan flufenamide hydrochloride (J1) and the excipient Polysorbate 80. The presence of the excipient Polysorbate 80 would increase the stability of the lyophilized pharmaceutical preparation. Further, the final preparation would be free, or essentially free of organic solvents, and therefore less toxic.

The invention provides a lyophilized preparation which is stable in dry form and soluble in an aqueous solution without presence of an organic solvent. While it previously was possible to prepare a lyophilized preparation of melphalan flufenamide alone, this preparation dissolved too slowly in aqueous solutions compared to the degradation time. Incorporation of an excipient in the lyophilized melphalan flufenamide preparation (via initial solution in an organic solvent) improves the reconstitution time considerably, but does not significantly alter the stability of reconstituted melphalan flufenamide. As a result, the time window for the reconstituted melphalan flufenamide is widened, and this improves the treatments of patients, e.g. by allowing for lower infusion rates, where needed. A preparation "without presence of an organic solvent" could include trace amounts of organic solvent, typically less than 0.5% (w/w).

The lyophilized pharmaceutical preparation of melphalan flufenamide or a pharmaceutically acceptable salt thereof as described herein, is a white, fluffy powder in contrast to a non-lyophilized melphalan flufenamide or a pharmaceutically acceptable salt thereof, which can be in the form of a dense, slightly yellowish powder.

Typically, lyophilization comprises four steps, pretreatment, freezing, primary drying, and secondary drying. In the pretreatment step, the substance to be lyophilized is made ready for the lyophilization e.g. by preparing a solution having the desired concentration or mixing the substance with further components in order to obtain an acceptable result. The freezing step may be performed in a freeze-drying flask in a bath cooled e.g. by mechanical refrigeration, dry ice and methanol, or liquid nitrogen. Freeze-drying machines are available for lyophilization in a larger scale. Usually, the freezing temperatures are between −50° C. and −80° C.

In the primary drying step, the pressure is lowered to the range of a few millibars, and heat may be supplied for the water to sublimate from the material. The amount of heat necessary can be calculated using the sublimating molecules' latent heat of sublimation. The duration of this period depends, but may last for days in order to preserve the materials structure.

The aim of the final secondary drying step is to remove any unfrozen water molecules. In this phase, the temperature may be as high as above 0° C., to break any physico-chemical interactions that have formed between the water molecules and the frozen material.

In the context of the present invention, it is to be understood that melphalan flufenamide or a pharmaceutically acceptable salt thereof, is lyophilized. The term "a lyophilized pharmaceutical preparation of a melphalan flufenamide or a pharmaceutically acceptable salt thereof", is therefore understood to mean that the melphalan flufenamide or a pharmaceutically acceptable salt thereof is lyophilized.

Further aspects of the present invention provide lyophilized melphalan flufenamide or a pharmaceutically acceptable salt thereof, a kit of parts comprising such melphalan flufenamide, methods for the preparation of such melphalan flufenamide or a pharmaceutically acceptable salt thereof, compositions comprising such lyophilized melphalan flufenamide or a pharmaceutically acceptable salt thereof and uses thereof.

"Lyophilization", "lyophilized" etc. may in the present context be used interchangeably with "freeze-drying", "freeze-dried" etc.

Examples of cytotoxic dipeptides that can be lyophilized as described herein are set forth in WO01/96367. The N-terminus of a molecule should preferably not be protected as amide or carbamate. This means that $R_4$ in formula I therein should preferably not be a protecting group, such as formyl, acetyl or propionyl, or benzoyl, as the protected form of the compound in general has a lower cytotoxic activity than the corresponding free form. Natural amino acids refer to amino acids that are normally existing and exerting their functions in living organisms. Modified amino acids refer to amino acids that in some way have been modified into a different chemical structure and chemical composition than a natural amino acid. An example of a natural cyclic amino acid is proline. Examples of aromatic amino acids are phenylalanine, tyrosine, tryptophan, and histidine.

The cytotoxic dipeptides, such as melphalan flufenamide, may also contain unnatural proportions of atomic isotopes at one or more of its atoms. For example, the compounds may be radiolabeled with radioactive isotopes, such as for example tritium ($^{3}H$), deuterium ($^{2}H$), iodine-125 ($^{125}I$) or carbon-14 ($^{14}C$).

The cytotoxic dipeptide melphalan flufenamide clearly differs from melphalan:
  Difference in structure (melphalan flufenamide is an ethyl ester at the C-terminal instead of the carboxylic acid in melphalan. Melphalan is thereby a zwitterion, but melphalan flufenamide is not).
  Difference in size (melphalan flufenamide is a dipeptide, i.e. approximately twice the size of melphalan).
  Difference in lipophilicity, where melphalan flufenamide is clearly more lipophilic.
  Difference in stability in aqueous solutions. Melphalan is 10 000 times more stable in aqueous solutions compared to J1. J1 is quickly hydrolyzed in water.
  Difference in degradation pathways. The main degradation pathway in melphalan flufenamide involves hydrolysis of the ethyl ester, while the main degradation in melphalan relates to the reactivity of the (chloro)alkyl groups.

Based on, but not limited to, the above differentiations, it is clear that teachings on melphalan and, in particular preparations and formulations thereof, do not apply to melphalan flufenamide and preparations and formulations thereof.

The inclusion of at least one excipient (such as Polysorbate 80 with its surfactant properties) provides lyophilized preparation that is stable as such and water-soluble without the presence of an organic solvent at a sufficient rate compared to the degradation rate, and is thereby useful in therapy and less toxic.

The lyophilized pharmaceutical preparation according to the invention may contain only melphalan flufenamide or a pharmaceutically acceptable salt thereof, or a mixture of melphalan flufenamide with one or more different cytotoxic dipeptides or pharmaceutically acceptable salts thereof. Further, the lyophilized pharmaceutical preparation may contain a mixture of two or more different pharmaceutically acceptable salts.

One aspect of the invention is a lyophilized pharmaceutical preparation, comprising
(i) melphalan flufenamide; and
ii) a combination of two or more excipients selected from the group comprising a polysorbate; a polyethylene glycol; β-cyclodextrin; α-cyclodextrin; hydroxypropyl-β-cyclodextrin; sulfobutylether-β-cyclodextrin; lactose; benzyl alcohol; disodium succinate; propylene glycol; Cremophor EL; Dimethyl sulfoxide; D-mannitol; Trehalose; Sucrose; and an amino acid.

Yet an aspect of the invention is a lyophilized pharmaceutical preparation, comprising:
(i) melphalan flufenamide hydrochloride (J1); and
(ii) a combination of two or more excipients selected from the group comprising a polysorbate; a polyethylene glycol; β-cyclodextrin; α-cyclodextrin; hydroxypropyl-β-cyclodextrin; sulfobutylether-β-cyclodextrin; lactose; benzyl alcohol; disodium succinate; propylene glycol; Cremophor EL; Dimethyl sulfoxide; D-mannitol; Trehalose; Sucrose; and an amino acid.

In one embodiment of this aspect, said combination of excipients is a mixture of Polysorbate 80 and PEG400.

Pharmaceutically acceptable salts for all aspects of the present invention may be, for instance, an acid-addition salt of a compound described herein which is sufficiently basic, for example, an acid-addition salt with, for example, an inorganic or organic acid, for example hydrochloric, hydrobromic, nitric, methansulphonic, sulphuric, phosphoric, trifluoroacetic, para-toluene sulphonic, 2-mesitylen sulphonic, citric, acetic, tartaric, fumaric, lactic, succinic, malic, malonic, maleic, 1,2-ethanedisulphonic, adipic, aspartic, benzenesulphonic, benzoic, ethanesulphonic or nicotinic acid.

In this document, when the term "melphalan flufenamide" is used, it is also intended to include pharmaceutically acceptable salt(s) thereof, even if this is not explicitly stated.

As mentioned hereinbefore, when melphalan flufenamide or a pharmaceutically acceptable salt thereof is lyophilized in the presence of a pharmaceutically acceptable excipient, such as any one selected from a polysorbate; a polyethylene glycol; β-cyclodextrin; α-cyclodextrin; hydroxypropyl-β-cyclodextrin; sulfobutylether-β-cyclodextrin; lactose; benzyl alcohol; disodium succinate; propylene glycol; Cremophor EL; Dimethyl sulfoxide; D-mannitol; Trehalose; Sucrose; and an amino acid; an unexpectedly high increase in solubility of the lyophilized pharmaceutical preparation can be obtained, which enables the direct dissolution of the lyophilized melphalan flufenamide in an aqueous solution, such as a physiologically acceptable solution. This is in contrast to a non-lyophilized melphalan flufenamide which is not possible to dissolve directly in an aqueous solution but that first has to be dissolved in an organic solvent prior to dilution in an aqueous solution. It is therefore provided herein a lyophilized pharmaceutical preparation comprising melphalan flufenamide or a pharmaceutically acceptable salt thereof, wherein melphalan flufenamide is lyophilized in the presence of an excipient. Preferably, said excipient is selected from polysorbate or polyethylene glycol, such as Polysorbate 80 or PEG400.

Melphalan flufenamide or a pharmaceutically acceptable salt thereof may be lyophilized in the presence of one or more of an excipient(s) (e.g. one, two, three, four, five, or more excipients). Examples of excipients that can be used as described herein include, without limitation, polysorbates such as Polysorbate 20, Polysorbate 40, Polysorbate 60, and Polysorbate 80; polyethylene glycols such as PEG 400 and PEG 300; β-cyclodextrin, α-cyclodextrin, sulfobutylether-β-cyclodextrin, hydroxypropyl-β-cyclodextrin, lactose, benzyl alcohol, disodium succinate, propylene glycol, Cremophor EL, dimethyl sulfoxide, D-mannitol, trehalose, sucrose and amino acids such as histidine.

In one aspect of the invention, the excipient is selected from any one of Polysorbate 80; PEG 400; β-cyclodextrin; α-cyclodextrin; hydroxypropyl-β-cyclodextrin; sulfobutylether-β-cyclodextrin; lactose; benzyl alcohol; disodium succinate; propylene glycol; PEG 300; Cremophor EL; Dimethyl sulfoxide; D-mannitol; Trehalose; Sucrose; and histidine.

In one aspect of the invention, the excipient is selected from Polysorbate 80; PEG 400; lactose; benzyl alcohol; disodium succinate; propylene glycol; PEG 300; Cremophor EL; Dimethyl sulfoxide; D-mannitol; Trehalose; Sucrose; and histidine, or a combination of two or more of said excipients.

In one embodiment of this aspect, the excipient is selected from Polysorbate 80 and PEG 400, or a combination of said two excipients.

The amount of excipient such as Polysorbate 80, PEG 400 or β-cyclodextrin, is typically about 10-100% by weight of the amount of melphalan flufenamide, such as 100, 90, 80, 70, 60, 50, 40, 30, 20 or 10% by weight of the amount of melphalan flufenamide.

In yet an aspect of the invention, the amount of the excipient, such as Polysorbate 80, PEG 400 or β-cyclodextrin, is typically about 10-50% by weight of the amount of melphalan flufenamide, such as 100, 90, 80, 70, 60, 50, 40, 30, 20 or 10% by weight of the amount of melphalan flufenamide.

In one embodiment of this aspect, the excipient represents Polysorbate 80 or PEG 400, and the amount thereof is typically about 10-50% by weight of the amount of melphalan flufenamide, such as 100, 90, 80, 70, 60, 50, 40, 30, 20 or 10% by weight of the amount of melphalan flufenamide.

Still an aspect of the invention is a lyophilized pharmaceutical preparation comprising
(i) melphalan flufenamide, or a pharmaceutically acceptable salt thereof; and
(ii) at least one excipient selected from the group comprising
Polysorbate 80; PEG 400; β-cyclodextrin; α-cyclodextrin; hydroxypropyl-β-cyclodextrin; sulfobutylether-β-cyclodextrin; lactose; benzyl alcohol; disodium succinate; propylene glycol; PEG 300; Cremophor EL; Dimethyl sulfoxide; D-mannitol; Trehalose; Sucrose; and histidine;
wherein the amount of the excipient is about 10-100% by weight of melphalan flufenamide.

In one embodiment of this aspect, the at least one excipient selected from Polysorbate 80 and PEG 400.

In another embodiment of this aspect, melphalan flufenamide is represented by melphalan flufenamide hydrochloride (J1).

Still an aspect of the invention is a lyophilized pharmaceutical preparation comprising
(i) melphalan flufenamide, or a pharmaceutically acceptable salt thereof; and
(ii) at least one excipient selected from the group comprising
Polysorbate 80; PEG 400; β-cyclodextrin; α-cyclodextrin; hydroxypropyl-β-cyclodextrin; sulfobutylether-β-cyclodextrin; lactose; benzyl alcohol; disodium succinate; propylene glycol; PEG 300; Cremophor EL; Dimethyl sulfoxide; D-mannitol; Trehalose; Sucrose; and histidine;
wherein the amount of the excipient is about 10-50% by weight of melphalan flufenamide hydrochloride (J1).

In one embodiment of this aspect, the at least one excipient selected from Polysorbate 80 and PEG 400.

In another embodiment of this aspect, melphalan flufenamide is represented by melphalan flufenamide hydrochloride (J1).

Yet an aspect of the invention is a lyophilized pharmaceutical preparation comprising
(i) melphalan flufenamide hydrochloride (J1); and
(ii) at least one excipient selected from the group comprising
Polysorbate 80; PEG 400; β-cyclodextrin; α-cyclodextrin; hydroxypropyl-β-cyclodextrin; sulfobutylether-β-cyclodextrin; lactose; benzyl alcohol; disodium succinate; propylene glycol; PEG 300; Cremophor EL; Dimethyl sulfoxide; D-mannitol; Trehalose; Sucrose; and histidine;
wherein the amount of the excipient is about 10-100% by weight of melphalan flufenamide hydrochloride (J1).

In one embodiment of this aspect, the at least one excipient selected from Polysorbate 80 and PEG 400.

Yet an aspect of the invention is a lyophilized pharmaceutical preparation comprising
(i) melphalan flufenamide hydrochloride (J1); and
(ii) at least one excipient selected from the group comprising
Polysorbate 80; PEG 400; β-cyclodextrin; α-cyclodextrin; hydroxypropyl-β-cyclodextrin; sulfobutylether-β-cyclodextrin; lactose; benzyl alcohol; disodium succinate; propylene glycol; PEG 300; Cremophor EL; Dimethyl sulfoxide; D-mannitol; Trehalose; Sucrose; and histidine;
wherein the amount of the excipient is about 10-50% by weight of melphalan flufenamide hydrochloride (J1).

In one embodiment of this aspect, the at least one excipient selected from Polysorbate 80 and PEG 400.

In one embodiment of the invention, the amount of excipient, such as Polysorbate 80 or PEG 400, may be up to the clinically acceptable amount.

In one embodiment of the invention, the amount of excipient, such as Polysorbate 80 or PEG 400, may be up to the clinically acceptable amount.

When used as the only excipient, the amount of Polysorbate 80 or PEG 400, is e.g. about 50% by weight of the amount of melphalan flufenamide hydrochloride (J1).

An aspect of the invention is a combination of the excipients Polysorbate 80 and PEG 400.

An aspect of the invention is a combination of the excipients Polysorbate 80, PEG 400 and β-cyclodextrin, such as 80% by weight of Polysorbate 80, 80% by weight of PEG 400 and 50% by weight of β-cyclodextrin, of the amount of melphalan flufenamide. A lyophilized pharmaceutical preparation of a melphalan derivative or a pharmaceutically acceptable salt thereof, may in accordance with the invention comprise one or more melphalan derivative(s) or a pharmaceutically acceptable salt(s) thereof, and one or more excipient(s) as defined herein.

As mentioned hereinbefore, one effect of the presence of an excipient during the lyophilization is that the resulting lyophilized pharmaceutical preparation comprising melphalan flufenamide, has an enhanced solubility in aqueous solutions, such as a physiologically acceptable solution, compared to when melphalan flufenamide is lyophilized without an excipient as described herein. In particular, the solubility in aqueous solutions of melphalan flufenamide when lyophilized in the presence of an excipient(s) is higher compared to the solubility of the non-lyophilized product. This increased solubility of melphalan flufenamide, in particular when lyophilized in the presence of an excipient as herein described, compared to the non-lyophilized product, has substantial advantages when it comes to administration of melphalan flufenamide to a patient.

Due to a low solubility of non-lyophilized melphalan flufenamide in aqueous physiologically acceptable solutions used for administration of the drug to a patient, it is necessary to first dissolve the non-lyophilized melphalan flufenamide in an organic solvent, such as DMA. Melphalan flufenamide is therefore often stored dissolved in DMA. It has previously not been possible to directly dissolve the melphalan flufenamide in an aqueous solution, but organic solvents have had to be used. Once dissolved in the organic solvent, this solution of melphalan flufenamide and organic solvent can be dissolved in physiologically acceptable solutions for administration to a subject.

As melphalan flufenamide is very toxic, in order to minimize the exposure of medical personnel to such drugs, special devices for transferring the drugs after dissolution in organic solvents to the solution for administration, are used. These transfer devices are often plastic tubings comprising polycarbonate. However, such tubings are sensitive to and may be destroyed by organic solvents, such as DMA. Therefore, in the cases where the drug to be administered is dissolved in such an organic solvent, it may not be possible to use the transfer device, and the dissolved drug instead has to be directly added to the physiologically acceptable solution used for administration just before the time of administration to the patient. This can be hazardous for the medical staff, who then are at risk being exposed to the toxic drug.

As mentioned above, lyophilization of melphalan flufenamide increases its solubility in physiologically acceptable solutions. This increase can be even more pronounced when melphalan flufenamide is lyophilized in the presence of one or more excipients. As described herein, when melphalan flufenamide is lyophilized in the presence of an excipient as disclosed herein, the solubility of melphalan flufenamide can be increased, in comparison to the non-lyophilized melphalan flufenamide. The use of an organic solvent, such as DMA, to first dissolve melphalan flufenamide can be avoided.

Melphalan flufenamide which has been lyophilized in the presence of at least one excipient, such as a polysorbate which for example may be Polysorbate 80; a polyethylene glycol which for example may be PEG 400 or PEG 300; β-cyclodextrin; α-cyclodextrin; hydroxypropyl-β-cyclodextrin; sulfobutylether-β-cyclodextrin; lactose; benzyl alcohol; disodium succinate; propylene glycol; Cremophor EL; Dimethyl sulfoxide; D-mannitol; Trehalose; Sucrose; or an amino acid such as histidine; or a combination of two or more of these excipients; can be directly dissolved in a physiologically acceptable solution, such as about 4.5-5.5 wt %, e.g. about 5%, glucose solution or an aqueous NaCl solution (e.g. about 0.9 wt % NaCl). Thereby, devices comprising polycarbonate and which are used for the administration of melphalan flufenamide are possible to use, minimizing the risk for exposing the medical personnel to the drug. Also, in this way administering the toxic DMA to the patient is avoided. This allows for directly preparing the solution comprising melphalan flufenamide at a concentration suitable for administration to the patient. Alternatively, a concentrated solution comprising a lyophilized pharmaceutical preparation of melphalan flufenamide in a physiologically acceptable solution may first be prepared and then transferred to the bag for infusion using the commonly used transfer devices.

Also, when melphalan flufenamide is dissolved in DMA, an adduct between the melphalan flufenamide and the DMA can be formed. By using a lyophilized pharmaceutical preparation provided in accordance with the invention, it is possible to dissolve the lyophilized melphalan flufenamide directly in a physiologically acceptable solution, avoiding first dissolving the melphalan flufenamide in DMA. Thereby, the formation of a DMA-melphalan flufenamide adducts can be avoided and neither the adduct nor the DMA have to be administered to the patient.

There is also provided a pharmaceutical composition comprising a lyophilized pharmaceutical preparation of melphalan flufenamide or pharmaceutically acceptable salt thereof as defined herein, optionally obtainable by the method for preparing such a lyophilized preparation disclosed herein. Such a pharmaceutical composition may further comprise a physiologically acceptable solution, such as an aqueous NaCl (e.g. about 0.9 wt %) or glucose solution (e.g. about 4.5-5.5 wt %, such as about 5 wt %, glucose). This pharmaceutical composition may be a concentrated solution intended for dilution before administration to a subject or as a solution enabling direct administration to a patient.

Due to the increased solubility of melphalan flufenamide after lyophilization in the presence of one or more excipients as described herein, it is possible to prepare a dissolved melphalan flufenamide solution, such as a pharmaceutical composition comprising a melphalan flufenamide or pharmaceutically acceptable salt thereof, which is substantially free from organic solvents such as DMA, dichloromethane, tetrahydrofuran, 2-methyl tetrahydrofuran, ethyl acetate, acetone, dimethylformamide, acetonitrile, dimethyl sulfoxide, dioxane, diethyl ether, acetic acid, n-butanol, isopropanol, n-propanol, tert-butanol, sec-butanol, methanol, ethanol, and acetic acid. By "substantially free" is in this document meant that the pharmaceutical composition comprises only trace amounts of an organic solvent, such as less than about a total of about 0.1 wt % of an organic solvent. In one aspect, the lyophilized preparation or the pharmaceutical composition does not contain any measurable amounts of an organic solvent. Such preparations would be less toxic and therefore more tolerated by a patient, ie giving less side effect such as vomiting, nausea or other general symptoms when infused.

In one aspect of the invention, there is provided a lyophilized pharmaceutical preparation as described herein, which is free, or substantially free from organic solvents.

The pharmaceutical composition may consist of a lyophilized pharmaceutical preparation as disclosed herein, comprising melphalan flufenamide or pharmaceutical salt thereof, and the physiologically acceptable solution, such as a glucose solution. As disclosed hereinbefore, the melphalan derivative may be melphalan flufenamide or a mixture of melphalan flufenamide and one or more different cytotoxic dipeptides, either lyophilized together or separately.

The pharmaceutical composition may be obtainable by dissolving melphalan flufenamide or a pharmaceutical salt thereof in a physiologically acceptable solution. A method for preparing a pharmaceutical composition comprising the step of dissolving the lyophilized pharmaceutical preparation comprising melphalan flufenamide or a pharmaceutically acceptable salt thereof in a physiologically acceptable solution is therefore also provided herein.

The wording a "physiologically acceptable solution" is herein defined, is an aqueous solution, such as a NaCl solution (such as about 0.9 wt-% NaCl) or glucose solution, such as about 4.5-5.5 wt-% glucose, e.g. about 5 wt-%, or another physiologically acceptable solution. Any such solution may optionally be buffered.

A pharmaceutical composition comprising lyophilized melphalan flufenamide and a physiologically acceptable solution for direct administration to a subject, generally comprises melphalan flufenamide at a concentration of about 1 mg/ml or less, such as about 0.2 mg/ml. However, the pharmaceutical composition may comprise melphalan flufenamide in a concentration of up to about 4 mg/ml for dilution in a physiologically acceptable solution before administration to a patient.

One aspect of the invention provides a method for preparing a lyophilized pharmaceutical preparation, whereby:
a) melphalan flufenamide, or a pharmaceutically acceptable salt thereof, is dissolved in an organic solvent to obtain a melphalan flufenamide solution;
b) water is added to the melphalan flufenamide solution in order to obtain an aqueous melphalan flufenamide solution, in a concentration of about 0.2-3.0 mg/ml;
c) at least one excipient selected from the group comprising a polysorbate; a polyethylene glycol; β-cyclodextrin; α-cyclodextrin; hydroxypropyl-β-cyclodextrin; sulfobutylether-β-cyclodextrin; lactose; benzyl alcohol; disodium succinate; propylene glycol; Cremophor EL; Dimethyl sulfoxide; D-mannitol; Trehalose; Sucrose and an amino acid is added to the melphalan flufenamide solution; and
d) the aqueous melphalan flufenamide solution containing excipient(s) is subjected to lyophilization.

In one embodiment of this aspect, there is provided a method, whereby:
a) melphalan flufenamide, or a pharmaceutically acceptable salt thereof, is dissolved in an organic solvent;
b) water is added to the solution obtained in step a) in order to obtain a solution of said melphalan flufenamide or a pharmaceutically acceptable salt thereof, in a concentration of about 0.2-3.0 mg/ml;
c) at least one excipient selected from the group comprising a polysorbate; a polyethylene glycol; β-cyclodextrin; α-cyclodextrin; hydroxypropyl-β-cyclodextrin; sulfobutylether-β-cyclodextrin; lactose; benzyl alcohol; disodium succinate; propylene glycol; Cremophor EL; Dimethyl sulfoxide; D-mannitol; Trehalose; Sucrose and an amino acid is added to the solution obtained in step b); and
d) the solution obtained in step c) is subjected to lyophilization.

The organic solvent may be selected from any one of ethanol, ethanol containing acid, glycerin, propylene glycol, benzyl alcohol, dimethylacetamide (DMA), N-methyl-2-pyrrolidone, isopropanol, n-butanol, tert-butanol, methyl tert-butyl ether, propylene glycol, dimethylsulfoxide, tetrahydrofuran, 2-methyl tetrahydrofuran, acetone, dimethylformamide, acetonitrile, dioxane, acetic acid, lactic acid, propionic acid, n-butanol, isopropanol, n-propanol, tert-butanol, sec-butanol, methanol, and a mixture of ethanol and water. Preferably, said organic solvent is ethanol.

The excipient may be selected from the group comprising Polysorbate 80; PEG 400; β-cyclodextrin; α-cyclodextrin; hydroxypropyl-β-cyclodextrin; sulfobutylether-β-cyclodextrin; lactose; benzyl alcohol; disodium succinate; propylene glycol; PEG 300; Cremophor EL; Dimethyl sulfoxide; D-mannitol; Trehalose; Sucrose; and histidine. Preferably, said excipient is selected from Polysorbate 80 and PEG 400.

The melphalan flufenamide in said methods is preferably melphalan flufenamide hydrochloride (J1).

An aspect of the present invention is a method for the preparation of a lyophilized pharmaceutical preparation as herein described, whereby
a) melphalan flufenamide, or a pharmaceutically acceptable salt thereof, is dissolved in an organic solvent;
b) water is added to the solution obtained in step a) in order to obtain a solution of said melphalan flufenamide or a pharmaceutically acceptable salt thereof, in a concentration of about 0.2-3.0 mg/ml;
c) at least one excipient as herein defined, is added to the solution obtained in step b); and
d) the solution obtained in step c) is subjected to lyophilization.

Preferably, said organic solvent is ethanol.

An aspect of the present invention is a method for the preparation of a lyophilized pharmaceutical preparation as herein described, whereby
a) melphalan flufenamide hydrochloride (J1), is dissolved in an organic solvent;
b) water is added to the solution obtained in step a) in order to obtain a solution of said melphalan flufenamide hydrochloride (J1), or a pharmaceutically acceptable salt thereof, in a concentration of about 0.2-3.0 mg/ml;
c) at least one excipient as herein defined, is added to the solution obtained in step b); and
d) the solution obtained in step c) is subjected to lyophilization.

Examples of organic solvents useful for dissolving melphalan flufenamide, or a pharmaceutically acceptable salt thereof in step a), may be any one selected from ethanol, ethanol containing acid, glycerin, propylene glycol, benzyl alcohol, dimethylacetamide (DMA), N-methyl-2-pyrrolidone, isopropanol, n-butanol, tert-butanol, methyl tert-butyl ether, propylene glycol, dimethylsulfoxide, tetrahydrofuran, 2-methyl tetrahydrofuran, acetone, dimethylformamide, acetonitrile, dioxane, acetic acid, lactic acid, propionic acid, n-butanol, isopropanol, n-propanol, tert-butanol, sec-butanol, methanol, and a mixture of ethanol and water.

An aspect of the present invention is a method for the preparation of a lyophilized pharmaceutical preparation as herein described, whereby
a) melphalan flufenamide, or a pharmaceutically acceptable salt thereof, is dissolved in an organic solvent selected from any one of ethanol, ethanol containing acid, glycerin, propylene glycol, benzyl alcohol, dimethylacetamide (DMA), N-methyl-2-pyrrolidone, isopropanol, n-butanol, tert-butanol, methyl tert-butyl ether, propylene glycol, dimethylsulfoxide, tetrahydrofuran, 2-methyl tetrahydrofuran, acetone, dimethylformamide, acetonitrile, dioxane, acetic acid, lactic acid, propionic acid, n-butanol, isopropanol, n-propanol, tert-butanol, sec-butanol, methanol, and a mixture of ethanol and water;
b) water is added to the solution obtained in step a) in order to obtain a solution of said melphalan flufenamide or a pharmaceutically acceptable salt thereof, in a concentration of about 0.2-3.0 mg/ml;
c) at least one excipient as herein defined, is added to the solution obtained in step b); and
d) the solution obtained in step c) is subjected to lyophilization.

An aspect of the present invention is is a method for the preparation of a lyophilized pharmaceutical preparation as herein described, whereby
a) melphalan flufenamide hydrochloride (J1), is dissolved in an organic solvent selected from any one of ethanol, ethanol containing acid, glycerin, propylene glycol, benzyl alcohol, dimethylacetamide (DMA), N-methyl-2-pyrrolidone, isopropanol, n-butanol, tert-butanol, methyl tert-butyl ether, propylene glycol, dimethylsulfoxide, tetrahydrofuran, 2-methyl tetrahydrofuran, acetone, dimethylformamide, acetonitrile, dioxane, acetic acid, lactic acid, propionic acid, n-butanol, isopropanol, n-propanol, tert-butanol, sec-butanol, methanol, and a mixture of ethanol and water;
b) water is added to the solution obtained in step a) in order to obtain a solution of said melphalan flufenamide hydrochloride (J1), or a pharmaceutically acceptable salt thereof, in a concentration of about 0.2-3.0 mg/ml;
c) at least one excipient as herein defined, is added to the solution obtained in step b); and
d) the solution obtained in step c) is subjected to lyophilization.

An aspect of the present invention is a method for the preparation of a lyophilized pharmaceutical preparation as herein described, whereby
a) melphalan flufenamide hydrochloride (J1), is dissolved in an organic solvent;
b) water is added to the solution obtained in step a) in order to obtain a solution of said melphalan flufenamide hydrochloride (J1), in a concentration of about 0.2-3.0 mg/ml;
c) at least one excipient as herein defined, is added to the solution obtained in step b); and
d) the solution obtained in step c) is subjected to lyophilization;
wherein said at least one excipient is selected from Polysorbate 80 and PEG400.

When ethanol containing acid is used for dissolving melphalan flufenamide or a pharmaceutically acceptable salt thereof in step a) in the method above, the acid can be HCl, in a concentration of for example 5-20 mM, or the HCl concentration may for example be 10 mM, in the ethanol.

When melphalan flufenamide or a pharmaceutically acceptable salt thereof is dissolved in ethanol and water, the concentration of ethanol may be about 10-100 vol-%, such as 10-90 vol-%, 50-90 vol-%, or about 70 vol-%.

The water used for dissolving and/or diluting samples of a lyophilized pharmaceutical preparation in accordance with the present invention, is sterile or purified water, or water for injection (WFI).

When ethanol is used for dissolving melphalan flufenamide or pharmaceutically acceptable salt thereof, the solution obtained in step a) is diluted in step b) so that the concentration of ethanol, is about 2%-100% by volume, such as about 2, 5, 10, 20, 30, 40, 50, 60, 70, 80, 90 or 100%, or such as 5-15%, or such as 5, 6, 7, 8, 9, 10, 11, 12, 13, 14 or 15%. Typically, the concentration of ethanol after the dilution step b) is about 9%.

The solution obtained in step b) may be sterile filtered before the lyophilization step c).

The lyophilization step c) comprises the typical freezing and primary and secondary drying steps as described herein. Information about how lyophilization is performed may be found e.g. in Rey, L. and May, J. *Freeze Drying/Lyophilization of Pharmaceutical and Biological Products* (2010), ISBN 978-1439B2575-4. In the freezing step, the sample is for example frozen in a bath of dry ice-acetone at a temperature of about −70° C. to −90° C., such as about −70° C., −75° C., −78° C., −80° C., −82° C., −85° C., −88° C. or −90° C. for example for 10 minutes to 120 minutes.

Alternatively, the sample may be frozen in a freezer at a temperature about −14° C. to −25° C., such as −14° C., −16° C., −18° C., −20° C., −22° C., or −25° C., for example for about 10 min to 24 hours. It is also possible to freeze the sample in liquid nitrogen.

Step c) may be performed by applying conventional techniques for lyophilization, see e.g. Rey, L. and May, J. *Freeze Drying/Lyophilization of Pharmaceutical and Biological Products* (2010), ISBN 978-1439B2575-4.

For example, in the primary drying step, the pressure can be lowered to about to about 0.1 mbar to 50 mbar, such as 1 mbar to 10 mbar. The temperature is typically below 0° C., such as −50 to 0° C., or −20 to −1° C., e.g. −50, −40, −30, −20, −10, or −5° C. This phase may for example last for 4 hours to 48 hours, e.g. 12 hours to 24 hours.

In the final secondary drying step, when most of the water has evaporated, the temperature may be as in the primary drying step or above 0° C.

When one or more excipients as defined herein are to be present during the lyophilization, these can be added in step b) prior to or after diluting the solution obtained in step a) and prior to performing the lyophilization. The excipients may be added in powder form but are generally added as an aqueous solution. The excipients can therefore be present during the lyophilization.

The present invention is also directed to a lyophilized pharmaceutical preparation as defined herein obtainable by the above disclosed method.

It is also provided herein a kit of parts comprising:
(i) a first container comprising a lyophilized pharmaceutical preparation comprising melphalan flufenamide as described herein; and
(ii) a second container comprising a physiologically acceptable solution, such as a NaCl solution (such as about 0.9 wt % NaCl) or a glucose solution, such as about 4.5-5.5 wt % glucose solution, e.g. about 5 wt % glucose solution, or other physiologically acceptable solution.

Such a kit may also comprise a device for mixing the contents of the two containers with each other and/or for transferring the resulting mixture to a device, such as a bag comprising a glucose solution, for the administration to a patient.

Such a kit may consist of the first container comprising a lyophilized pharmaceutical preparation comprising melphalan flufenamide as described herein and the second container comprising the physiologically acceptable solution. Melphalan flufenamide in the kit may also be in admixture with a pharmaceutically acceptable carrier and/or excipient. One example is 5% glucose with e.g. 1% albumin or another protein or compound. The amount of physiologically acceptable solution may either be a small amount in order to prepare a concentrated solution of the lyophilized pharmaceutical preparation comprising melphalan flufenamide, or a larger amount in order to enable the preparation of a solution having the desired concentration for administration to a patient. Alternatively, the kit may comprise both a container comprising a physiologically acceptable solution for preparing a concentrated solution of the infusion, comprising a larger amount of a physiologically acceptable solution for preparation of the more diluted solution for administration to a subject.

A lyophilized pharmaceutical preparation, pharmaceutical composition or kit provided herein may comprise only melphalan flufenamide or a pharmaceutically acceptable salt thereof as an antitumoral agent. However, melphalan flufenamide may also be combined with one or more antitumoral agents, such as other antitumoral substances such as gemcitabine, etoposide, doxorubicine or taxanes or other therapeutically effective substances. When combined with other antitumoral agents these may either be mixed with melphalan flufenamide or pharmaceutically acceptable salt thereof before lyophilisation and consequently lyophilized together with melphalan flufenamide or pharmaceutically acceptable salt thereof or combined with the lyophilized melphalan flufenamide or pharmaceutically acceptable salt thereof after lyophilisation, such as in a kit or a pharmaceutical composition. Lyophilized melphalan flufenamide may also be mixed with one or more antitumoral substances in dry form, even though not lyophilized, after lyophilisation of melphalan flufenamide or pharmaceutically acceptable salt thereof.

Melphalan flufenamide provided herein have a cytotoxic activity and may therefore be used in the prevention and/or treatment of cancer as described elsewhere (see e.g. WO 01/96367). A reduction of tumor cell survival of these compounds was in WO 01/96367 demonstrated for different hematological and/or solid tumors, e.g. lung cancer, myeloma, lymphoma, leukemia, breast cancer, and ovarian carcinoma. Further, these compounds were in WO 01/96367 demonstrated to circumvent melphalan resistance. These compounds may therefore be used in the prevention and/or treatment of cancer, reducing tumor growth and/or killing tumor cells. Thus, the compounds may be used for curing and/or prolonging the survival of patients afflicted with cancer diseases.

Also provided herein is the lyophilized pharmaceutical preparation, kit or pharmaceutical composition as disclosed and claimed herein, for use as a medicament. The invention is also directed to such a lyophilized pharmaceutical preparation, kit or pharmaceutical composition, for use in the treatment and/or prevention of cancer, such as ovarian cancer, lung cancer, bladder cancer, mesothelioma, multiple myeloma, breast cancer and/or any other solid or hematological cancer.

An aspect of the present invention is the use of a lyophilized pharmaceutical preparation, kit or pharmaceutical composition as disclosed and claimed herein, for the preparation of a medicament for the treatment and/or prevention of cancer, such as ovarian cancer, lung cancer, bladder cancer, mesothelioma, multiple myeloma, breast cancer and/or any other solid or hematological cancer.

Yet an aspect of the present invention provides a lyophilized pharmaceutical preparation, kit or pharmaceutical composition comprising melphalan flufenamide hydrochloride (J1) in combination with another drug useful in the treatment of cancer, for use in treatment and/or prevention of cancer, such as ovarian cancer, lung cancer, bladder cancer, mesothelioma, multiple myeloma, breast cancer and/or any other solid or hematological cancer.

Yet an aspect of the present invention is a method for the treatment of and/or prevention of cancer, such as ovarian cancer, lung cancer, bladder cancer, mesothelioma, multiple myeloma, breast cancer and/or any other solid or hematological cancer. The method can comprise the administration of a lyophilized pharmaceutical preparation, a kit or a pharmaceutical composition as provided herein in a therapeutically effective dose to a subject in need thereof. The subject is typically a human or a domestic animal.

Yet an aspect of the present invention is a method for the treatment of and/or prevention of cancer, such as ovarian cancer, lung cancer, bladder cancer, mesothelioma, multiple myeloma, breast cancer and/or any other solid or hematological cancer, wherein the lyophilized pharmaceutical preparation, a kit or a pharmaceutical composition comprising melphalan flufenamide hydrochloride (J1) is provided in a therapeutically effective dose to a subject in need thereof, in combination with another drug, useful in the treatment of cancer. The subject is typically a human or a domestic animal.

The administration of a lyophilized pharmaceutical preparation, a kit or a pharmaceutical composition to a subject in need thereof may take place by intravenous injections. It is also possible to administer lyophilized melphalan flufenamide or a pharmaceutical composition comprising such lyophilized melphalan flufenamide in body cavities, such as instillation in the bladder, or in peritoneal or pleural cavities.

Melphalan flufenamide or a pharmaceutically acceptable salt thereof may be administered in an amount of about 20-130 mg, such as 30-75 mg, for example 50 mg total amount of melphalan flufenamide per administration. The pharmaceutical composition or kit provided herein comprising melphalan flufenamide may therefore have an amount of lyophilized melphalan flufenamide such that this amount can be administered.

Lyophilized melphalan flufenamide or a pharmaceutically acceptable salt thereof may be administered daily, every second or third day, weekly, every second, third or $4^{th}$ week or even as a high single dose (e.g. before transplantation) depending on the subject and cancer form to be treated.

The wording "prevention" as used herein, is intended to include therapy in a patient that has been subjected to chemotherapy against any cancer form as herein described, and who is subjected to continued therapy with the aim of preventing any methastasis occurring from said cancer.

Yet an aspect of the present invention provides use of an excipient selected from the group comprising Polysorbate 80; PEG 400; β-cyclodextrin; α-cyclodextrin; hydroxypropyl-β-cyclodextrin; sulfobutylether-β-cyclodextrin; lactose; benzyl alcohol; disodium succinate; propylene glycol; PEG 300; Cremophor EL; Dimethyl sulfoxide; D-mannitol; Trehalose; Sucrose; and histidine, in a lyophilized preparation of melphalan flufenamide, or a pharmaceutically acceptable salt thereof, for decreasing the reconstitution time of the lyophilized preparation of melphalan flufenamide, or a pharmaceutically acceptable salt thereof, when reconstituted in an aqueous solvent.

Said melphalan flufenamide, or a pharmaceutically acceptable salt thereof, is preferably melphalan flufenamide hydrochloride (J1).

Said excipient is preferably selected from Polysorbate 80 and PEG 400.

Said melphalan flufenamide, or a pharmaceutically acceptable salt thereof, is preferably dissolved in ethanol prior to subjecting said melphalan flufenamide to said excipient.

In this document "lyophilization", "freeze-drying", "lyophilized", "freeze-dried", and the like may be used interchangeably.

Polysorbate 80 (having the chemical name Polyoxyethylene 20 sorbitan monooleate and the CAS registry number 9005-65-6) is commercially available from e.g. Fluka or Sigma-Aldrich.

PEG 400 has the empirical formula $HOCH_2(CH_2OCH_2)_m CH_2OH$, where m is 8.7, and the average molecular weight is 380-420, and is commercially available from e.g. Fluka or Sigma-Aldrich.

PEG 300 has the empirical formula $HOCH_2(CH_2OCH_2)_m CH_2OH$, where m is 6.4, and the average molecular weight is 285-315, and is commercially available from e.g. Fluka or Sigma-Aldrich.

Cremophor EL® is a trade mark sold by Sigma-Aldrich, and is Polyoxyethylene castor oil having the CAS Registry Number 61791-12-6.

Exemplary cytotoxic dipeptides that can be used as described herein are also disclosed in WO01/96367 and can have the formula V

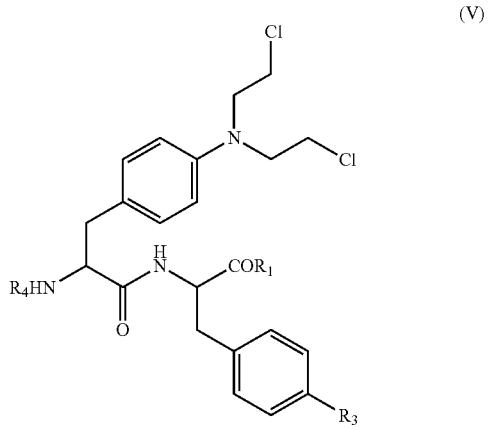

wherein
$R_1$ is alkyloxy, cycloalkyloxy, aryloxy, arylalkyloxy, $NH_2$, alkylamino, cycloalkylamino or arylamino;
$R_3$ is $NH_2$, OH, O-alkyl, N-alkyl, O-acyl, NH-acyl, $N(CH_2CH_2Cl)_2$, $NO_2$, F, $CF_3$ or H; and
$R_4$ is a natural or modified cyclic or aromatic amino acid, or H; as well as pharmaceutically acceptable salts thereof.

Also, cytotoxic peptides that can be used as described herein include peptides of the formula I or V, wherein $R_3$ is F. Dipeptides are examples of peptides of the formula I or V, wherein $R_1$ is alkyloxy; $R_3$ is F, $CF_3$, H, OH, O-alkyl, $NO_2$, $N(CH_2CH_2Cl)_2$, NH-acyl or $NH_2$; and $R_4$ is H.

Tripeptides are example of peptides of the formula I or V, wherein $R_1$ is alkyloxy; $R_3$ is F, $CF_3$, H, OH, O-alkyl, NH-acyl, $NO_2$, $N(CH_2CH_2Cl)_2$ or $NH_2$; and $R_4$ is a natural or modified cyclic or aromatic amino acid.

Melphalan flufenamide, or a pharmaceutically acceptable salt thereof, may be prepared as disclosed in WO 01/96367, which disclosure is incorporated by reference. Example 1 of WO 01/96367 discloses a synthetic procedure for making melphalan flufenamide (L-melphalanyl-L-p-fluorophenylalanine ethyl ester), as well as its hydrochloride salt-melphalan flufenamide hydrochloride J1 (L-melphalanyl-L-p-fluorophenylalanine ethyl ester, compound J1), which disclosure is incorporated herein.

The dipeptide derivatives disclosed in WO01/96367 can be synthesised from tert-butoxycarbonyl(Boc)-protected melphalan as disclosed therein and can be lyophilized and used as described herein. Also, WO01/96367 discloses the preparation of tripeptide derivatives, in which Boc-protected amino acids were coupled to the melphalan containing dipeptide derivative using EDC/NMM/HOBt as coupling reagents (EDC is triethylamine or 1-[3-dimethylamino)propyl]-3-ethylcarbodiimide hydrochloride, NMM is N-methylmorpholine and HOBt is 1-hydroxybenzotriazole). Such tripeptide derivatives may be lyophilized and used as described herein.

Figure 7A:
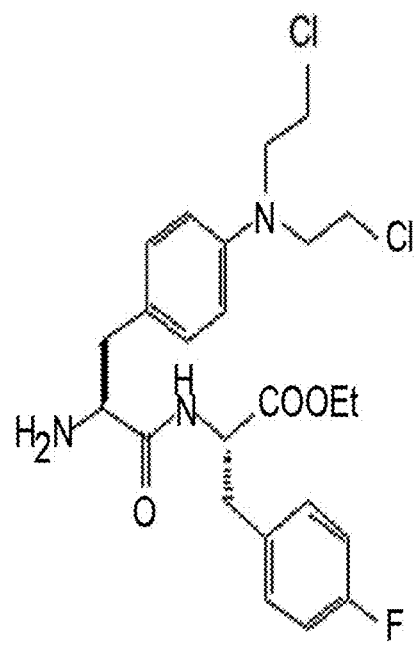
FIGS. 7A-C contain structural formulas for melphalan flufenamide (L-melphalanyl-L-p-fluorophenylalanine ethyl ester) (J1), L-melphalanyl-L-p-fluorophenylalanine isopropyl ester (JV28), and L-prolinyl-L-melphalanyl-L-p-fluorophenylalanine ethyl ester (J3), respectively.
Figure 7B:
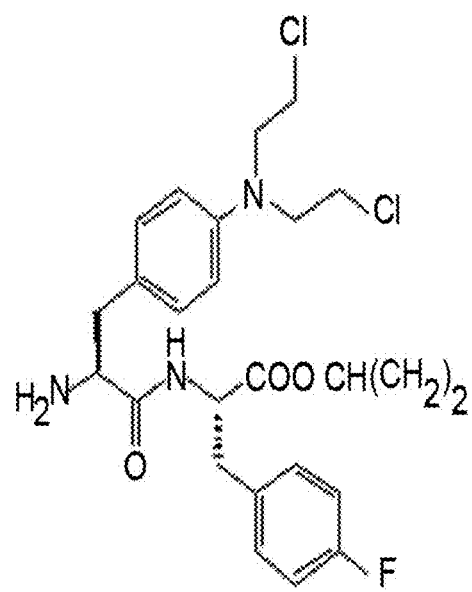
Figure 7C:
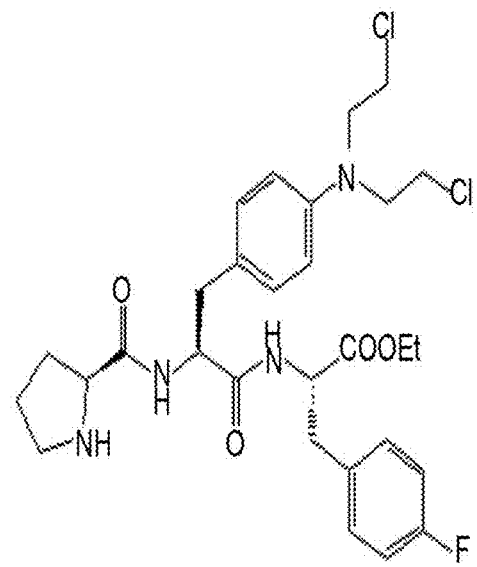

Examples of derivatives of melphalan that can be lyophilized and used as described herein in all aspects include, without limitation, melphalan flufenamide, L-melphalanyl-L-p-fluorophenylalanine isopropyl ester (JV28), L-prolinyl-L-melphalanyl-L-p-fluorophenylalanine ethyl ester (J3) (FIG. 7) and pharmaceutically acceptable salts thereof. These compounds are disclosed previously in WO01/96367, which also provides methods for their preparation. Melphalan flufenamide, JV28 and J3 may be transformed into melphalan in the body. In WO 01/96367, these derivatives were demonstrated to have an increased cell killing activity against tumors, even when used at lower concentrations than melphalan. In addition, melphalan resistance could be circumvented.

The invention will be further described by way of the following examples, which do not limit the scope of the invention.

EXPERIMENTAL SECTION

Example 1: Lyophilization of Melphalan Flufenamide Hydrochloride (J1) Under Different Conditions It this experiment lyophilization of melphalan flufenamide hydrochloride (J1), under various conditions was tested.

Example 1A

Weighed amounts of J1 were dissolved in various volumes of deionized water in ultrasound bath with slight heating to get clear solutions. The samples were frozen in a bath of dry ice-acetone (−78° C., samples A1-A3) or in a freezer at −16° C. (samples B1-B3). Freeze-drying was then conducted for 16 h at a pressure of 1 mbar at room temperature with a dry ice-acetone (−78° C.) trap between the drying flask and the pump.

The visual appearance after drying was as summarized in Table 1.

TABLE 1

Six different solutions of J1 at various freeze concentrations or temperatures.

| Exp no | mg J1 | mL water | conc (mg/mL) | appearance after drying |
|---|---|---|---|---|
| J1A1 | 2.4 | 6 | 0.4 | white fluffy |
| J1A2 | 2.7 | 27 | 0.1 | white fluffy - some incompletely dry |
| J1A3 | 2.5 | 10 | 0.25 | white fluffy |
| J1B1 | 2.7 | 6.75 | 0.4 | white solid |
| J1B2 | 2.5 | 25 | 0.1 | light yellow powder |
| J1B3 | 2.8 | 11.2 | 0.25 | white fluffy |

Example 1B

Samples of the dried compounds were dissolved in 50% aqueous acetonitrile and analyzed by HPLC (ACE-column, C8, 50×3 mm, 10-97% $CH_3CN$ in 3 min, 1 mL/min). In one case (J1A1) the aqueous solution was analyzed by HPLC before freeze-drying (J1A1-start). The purities after drying were as summarized in Table 2.

TABLE 2

Purity after freeze drying. Rt = Retention time

| Exp no | J1:Rt 2.27 (%) | Rt 1.87 (%) | Rt 1.44 (%) |
|---|---|---|---|
| J1A1-start | 88 | 12 | |
| J1A1 | 79 | 21 | |
| J1A2 | 80 | 20 | |
| J1A3 | 41 | 45 | 14 |
| J1B1 | 34 | 42 | 25 |
| J1B2 | 36 | 43 | 21 |
| J1B3 | 79 | 21 | |

Example 1

Next it was tested to use either slightly acidic water (for example 0.01% HCl) to enhance the speed of dissolution or to first dissolve J1 in ethanol, before adding water (neutral or slight acidic).

Three samples of J1 were prepared by dissolving melphalan flufenamide (ca 3 mg) in 70% aq. ethanol (0.5 mL). The solutions were diluted with 5 mM HCl to give a concentration of 0.4 mg/mL. Since melphalan flufenamide dissolved rapidly in aq. ethanol it was not necessary to use ultrasound bath or heating to get a clear solution. The solutions were then frozen in a bath of dry ice-acetone (−78° C.) trap between the drying flask and the pump. The visual appearance after drying was as summarized in Table 3.

TABLE 3

Three replicates of J1 dissolved in ethanol and acid.

| Exp no | mg J1 | mL HCl | conc (mg/mL) | appearance after drying |
|---|---|---|---|---|
| J1C1 | 3.0 | 7.0 | 0.4 | white solid some of which adhered to the glass |
| J1C2 | 3.2 | 7. | 0.4 | white solid some of which adhered to the glass |
| J1C3 | 2.9 | 6.75 | 0.4 | white solid some of which adhered to the glass |

Example 1D

Two HPLC runs were done on each sample: one from the solid compound that could be removed from the flask and one by dissolving the remainder in compound in the flask (table 4).

TABLE 4

Purity after freeze drying.

| Exp no | J1:Rt (%) | Rt (%) | Rt (%) |
|---|---|---|---|
| Run 1 | | | |
| J1C1 | 2.25 (97%) | 2.32 (3%) | |
| J1C2 | 2.24 (97%) | 1.87 (1%) | |
| J1C3 | 2.22 (99%) | 1.87 (1%) | 1.98 (1%) |
| Run 2 | | | |
| J1C1 | 2.25 (100%) | | |
| J1C2 | 2.25 (95%) | 1.88 (3%) | 1.98 (2%) |
| J1C3 | 2.25 (97%) | 1.87 (3%) | |

In conclusion, by dissolving J1 in 70% ethanol, diluting with 5 mM HCl and freeze-drying three samples were obtained with purity >95%.

Example 1E

It was then tested to omit the acid and instead dilute the ethanol with deionized water. Three samples of J1 were prepared by dissolving J1 (ca 3 mg) in 70% aq. ethanol (0.5 mL) at room temp. The solutions were diluted with deionized water to give a concentration of 0.4 mg/mL. The solutions were then frozen in a bath of dry ice-acetone (−78° C.). Freeze-drying was then conducted over 16 h at a pressure of 1 mbar at room temperature with a dry ice-acetone (−78° C.) trap between the drying flask and the pump. The visual appearance after drying was as summarized in Table 5 and the purities in Table 6.

TABLE 5

Three replicates of J1 dissolved in ethanol and water.

| Exp no | mg J1 | mL water | conc (mg/mL) | appearance after drying |
|---|---|---|---|---|
| J1D1 | 3.15 | 7.37 | 0.4 | white fluffy solid |
| J1D2 | 3.11 | 7.27 | 0.4 | white fluffy solid |
| J1D3 | 3.17 | 7.42 | 0.4 | white fluffy solid |

TABLE 6

Purity after freeze drying.

| Exp no | J1:Rt (%) |
|---|---|
| J1D1 | 2.26 (ca 100%) |
| J1D2 | 2.26 (ca 100%) |
| J1D3 | 2.25 (ca 100%) |

By dissolving J1 in 70% ethanol, diluting with water and freeze-drying; three replicate samples were obtained with the same purity as the starting material.

Example 2: Effect of Excipients on the Dissolution Rate of Lyophilized Melphalan Flufenamide In this experiment the effect on speed of dissolution by adding excipients to the freeze-drying process of melphalan flufenamide hydrochloride (J1) was tested. The following excipients were used, all of which are common formulation agents Generally Considered As Safe (GRAS) according to the FDA (US Food and Drug Administration):

D-mannitol, trehalose and sucrose;
Trizma hydrochloride and L-histidine;
Polysorbate 80, β-cyclodextrin;
J1 was used in all experiments.
D-Mannitol, was bought from Sigma no. 33440;
D-(+)-Trehalose dihydrate, was bought from Sigma no. T9449-25 g;
Trizma hydrochloride, was bought from Sigma no. T3253-100 g;
β-Cyclodextrin hydrate, was bought from Sigma no. 856088-5 g;
Polysorbate 80, was bought from Fluka 59924-100 g.

Freeze-drying was performed on a Leybold Lyovac GT2 equipment. LCMS (Liquid chromatography-mass spectrometry) was run on a HP1100-system using acetonitrile-0.1% trifluoroacetic acid in water as eluent. An ACE-column C8, 50×3 mm and a gradient 10-97% acetonitrile in 3 min was used. The filter vials were from Whatman, Mini-UniPrep, 0.45 μm.

(i) Method A, Freeze-Drying

Melphalan flufenamide (30.1 mg) was dissolved in 5 mL of 70% ethanol with 1 mM HCl, total dissolution within 12 min at 18-19° C. The solution was diluted with water (70 mL) and distributed (10 mL) into 250 mL round bottomed flasks with and without excipient (eg β-cyclodextrin, 9 mg). When all material had dissolved, the solutions were frozen by immersion in a dry-ice/acetone bath at −78° C. The frozen solutions were then freeze-dried at <0.1 mbar overnight and room temperature, evaporation keeping the samples frozen until dryness.

(ii) Method A, Speed of Dissolution Measurement

A 5% glucose solution (10 mL) was added in one portion at 18.5-19° C. to the freeze-dried material and stirred with a magnet. Aliquots (ca 0.3 mL) was taken with 1-mL syringe at various times and filtered through a filter vial (0.45 □m). The filtrate (8 □L) was analyzed by HPLC.

(iii) Method B, Freeze-Drying

Melphalan flufenamide (10.2 mg) was dissolved in 1.67 mL of 70% ethanol with 5 mM HCl, total dissolution within 5 min at 25° C. The solution was diluted with water (23.3 mL) and distributed (10 mL) into flasks with and without excipients (e.g. β-cyclodextrin, 9 mg). The solution of J1 and excipient was dispensed into plastic vials with a fitting insert 0.45 μm filter (0.25 mL to each vial). The vials were frozen by immersion in a dry-ice/acetone bath at −78° C. and then kept at −20° C. overnight in a rack fitting the vials. The frozen vials were covered by alumina foil to prevent cross-contamination and kept in the rack precooled to −20° C., while exposing the rack in a desiccator to <0.1 mbar overnight, evaporation keeping the samples frozen until dryness.

(iv) Method B, Speed of Dissolution Measurement

A 5% glucose solution (0.5 mL) was added, which contained an internal standard (3-methoxybenzoic acid, 0.08 mg/mL). After various times (15 s-12 min) the contents of the vials were filtered, the filtrate directly transferred to glass vials to prevent leaking of undissolved material into the filtrate and 8 μL of the filtrate injected into the LCMS.

Determination of Dissolution Speed

In a first approach, Method A, aqueous solutions of J1 with different additives were freeze-dried in round bottomed flasks. To each freeze dried compound, a glucose solution was added with controlled stirring. Small aliquots were withdrawn with a syringe at specific times and filtered through a 0.45 μm GHP syringe filter. The degree of dissolution of J1 in the filtrate was then determined by HPLC. This method was used with freeze-dried melphalan flufenamide alone and together with D-mannitol, trehalose, sucrose, Polysorbate 80 and β-cyclodextrin. The result of these tests showed that J1 was completely dissolved within 2-4 min regardless of excipient (see FIG. 1, no excipients, and FIG. 2, with excipients. See also Table 7). In fact, the dissolution rate for J1 lyophilized with excipients was actually faster than could be measured using this method.

TABLE 7

Excipient additions to J1 (4 mg) on freeze-drying, Method A.

| Freeze dried material | Ratio J1:additive (mg J1:mg additive) | Number of experiments |
|---|---|---|
| D-Mannitol | 4:2 | 1 |
| D-Mannitol | 4:10 | 2 |
| Trehalose | 4:2 | 1 |
| Trehalose | 4:10 | 2 |

TABLE 7-continued

Excipient additions to J1 (4 mg) on freeze-drying, Method A.

| Freeze dried material | Ratio J1:additive (mg J1:mg additive) | Number of experiments |
|---|---|---|
| Sucrose | 4:10 | 1 |
| β-Cyclodextrin | 4:9 | 1 |
| β-Cyclodextrin | 4:18 | 2 |
| Polysorbate 80 | 4:0.05 | 1 |
| Polysorbate 80 | 4:0.265 | 2 |

To improve the precision and enable measurement of dissolution at shorter intervals, Method B was developed. In this method, aqueous solutions of melphalan flufenamide and excipients (see Table 2) were added to 2 mL plastic vials and freeze-dried. Then a glucose solution with internal standard 3-methoxybenzoic acid was added without stirring. After varying times (15 s-6 min) the contents of the vial was filtered with a 0.45 μm GHP vial insert, the filtrate transferred to a glass vial and the degree of dissolution of melphalan flufenamide hydrochloride (J1) determined by HPLC with internal standard. The lack of stirring made possible a slower dissolution process, both more clinically relevant and easier to measure the kinetics of.

Figure 3:
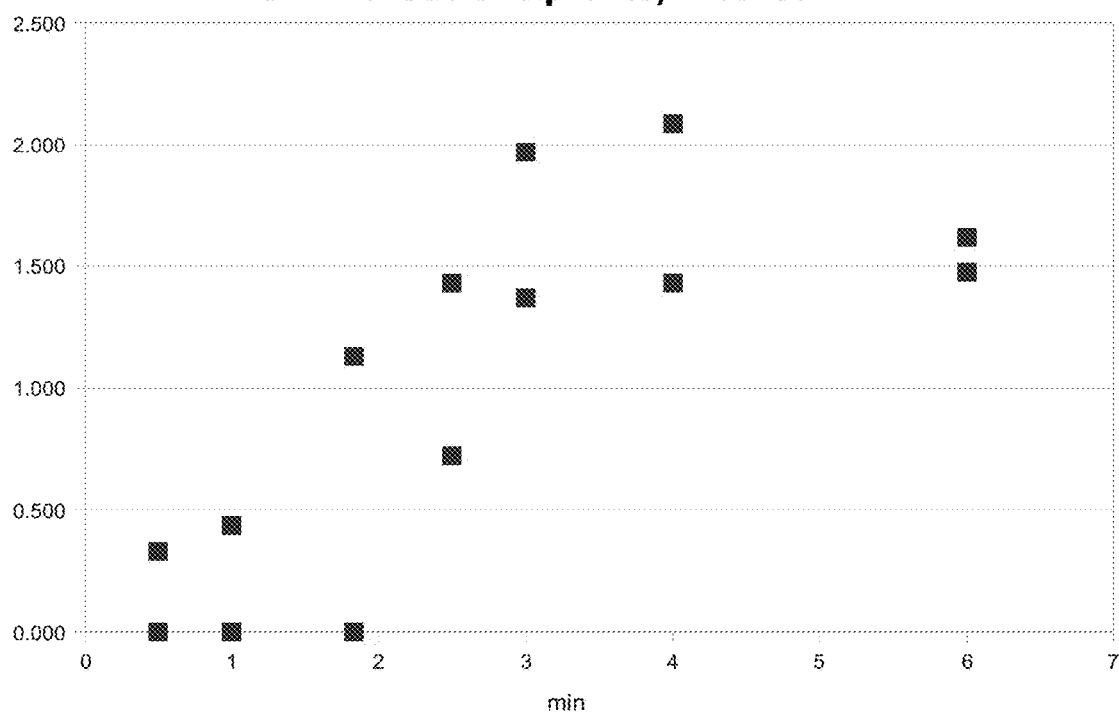
FIG. 3 is a graph of dissolution speed measurement of melphalan flufenamide without excipients by method B according to Example 2. Samples were withdrawn at the indicated time points and the amount of dissolved melphalan flufenamide was determined by HPLC. The y-axis shows the amount of melphalan flufenamide in mg/ml.
Figure 4A:
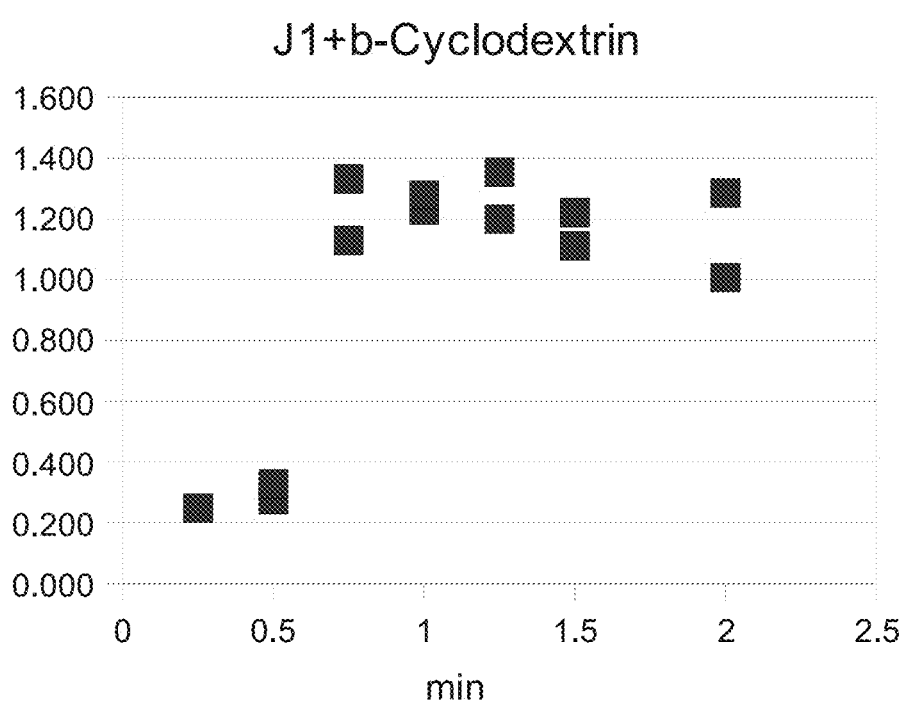
FIGS. 4A-E contain graphs of dissolution speed measurements of melphalan flufenamide lyophilized in the presence of excipients as indicated in the figures by method B. Samples were withdrawn at the indicated time points and the amount of dissolved melphalan flufenamide was determined by HPLC. The y-axis shows the amount of melphalan flufenamide in mg/ml.
Figure 4B:
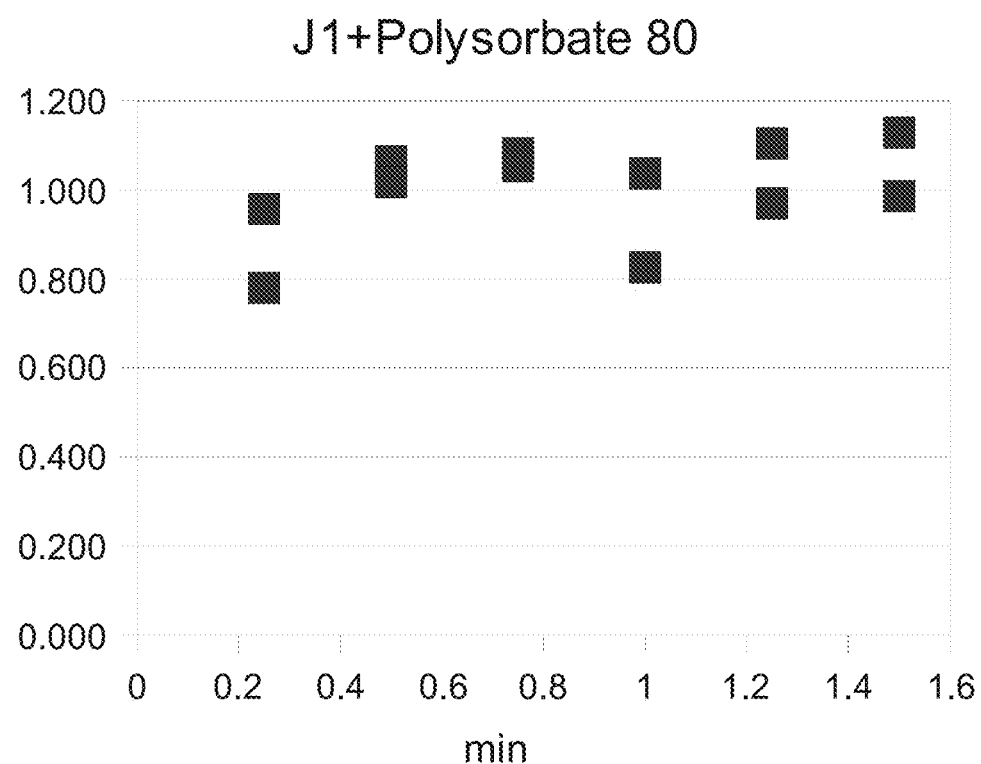
Figure 4C:
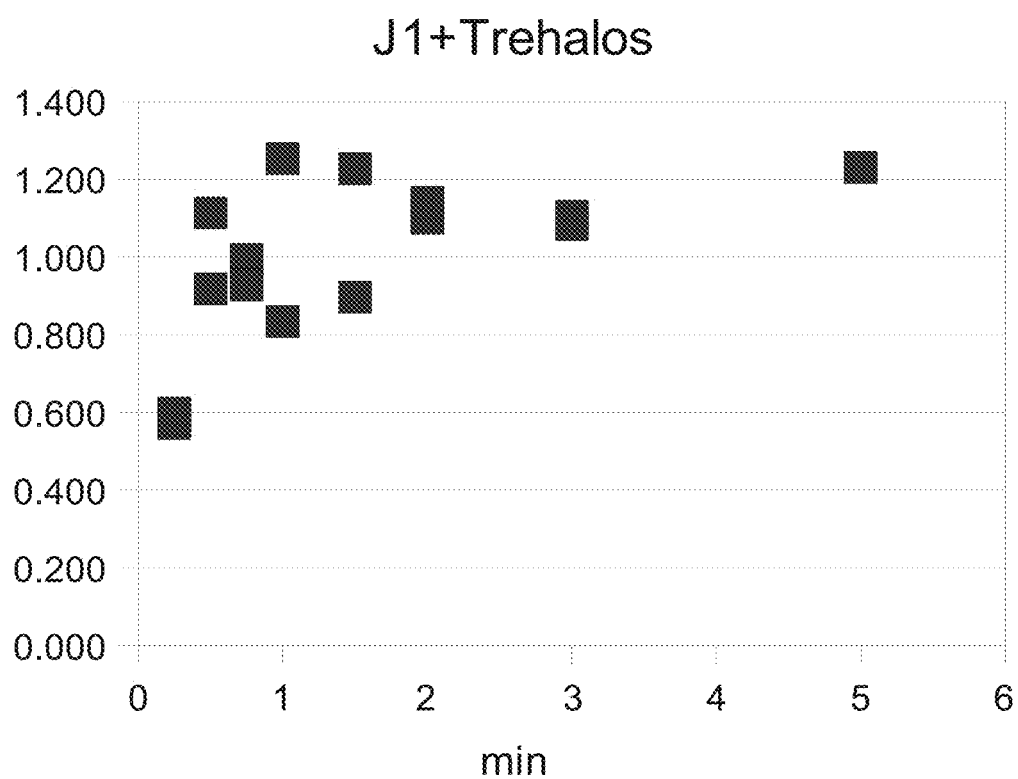
Figure 4D:
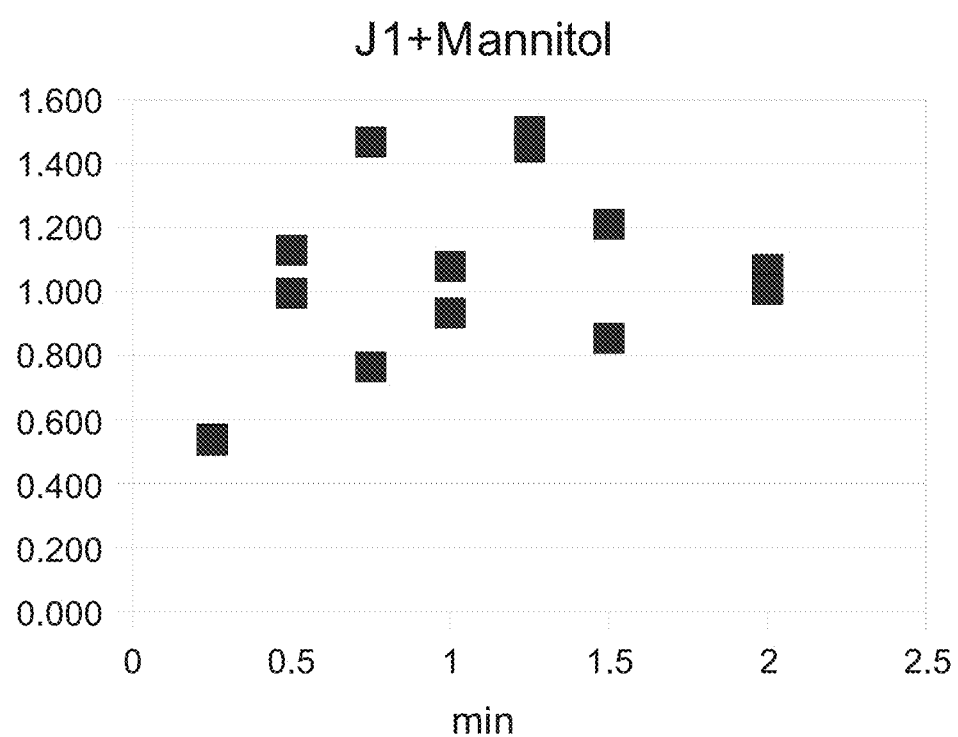
Figure 4E:
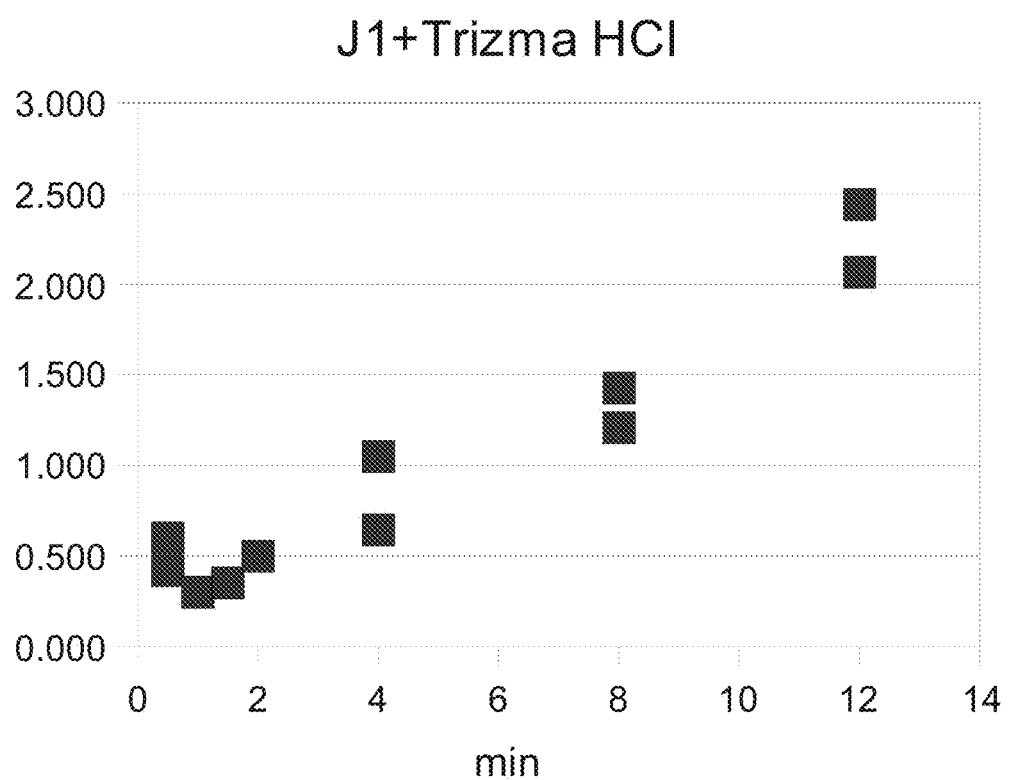
Figure 5A:
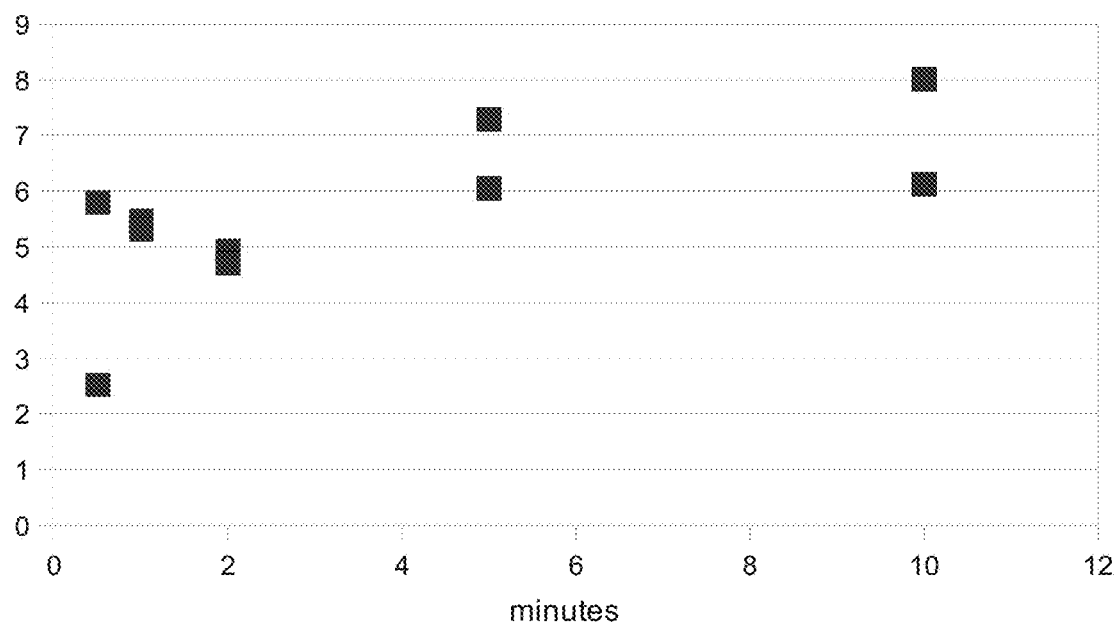
FIGS. 5A-D contain graphs of dissolution speed measurements as follows, A: melphalan flufenamide lyophilized without Polysorbate 80; B melphalan flufenamide lyophilized in the presence of 10% Polysorbate 80; C melphalan flufenamide lyophilized in the presence of 50% Polysorbate 80; D melphalan flufenamide lyophilized in the presence of 100% Polysorbate 80. Amounts are relative to the amount of melphalan flufenamide. The y-axis shows the amount dissolved melphalan flufenamide relative to the internal standard as determined using HPLC.
Figure 5B:
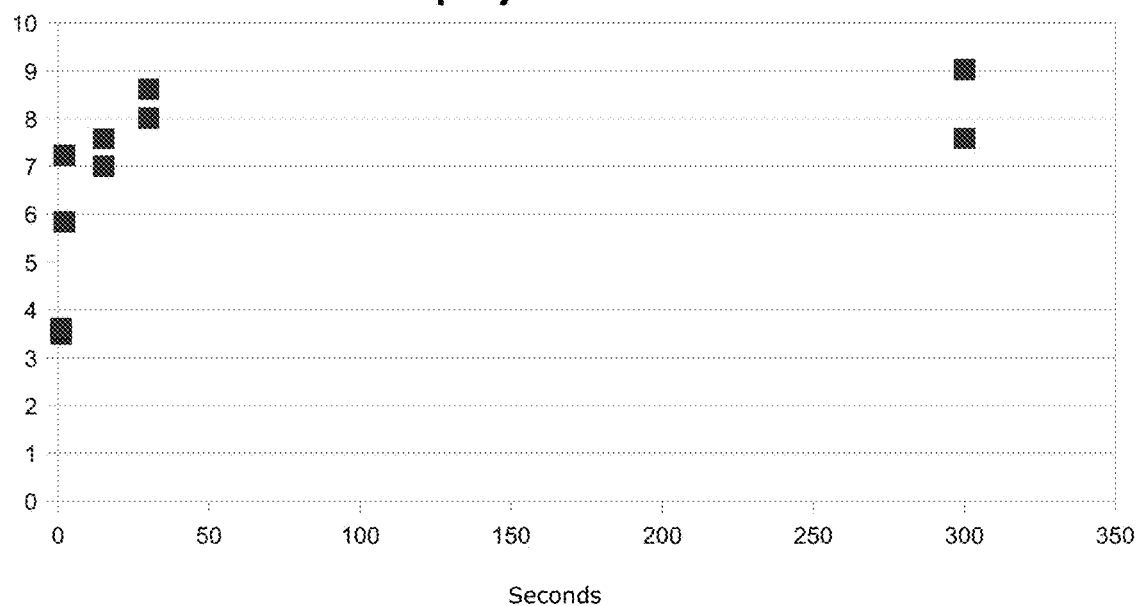
Figure 5C:
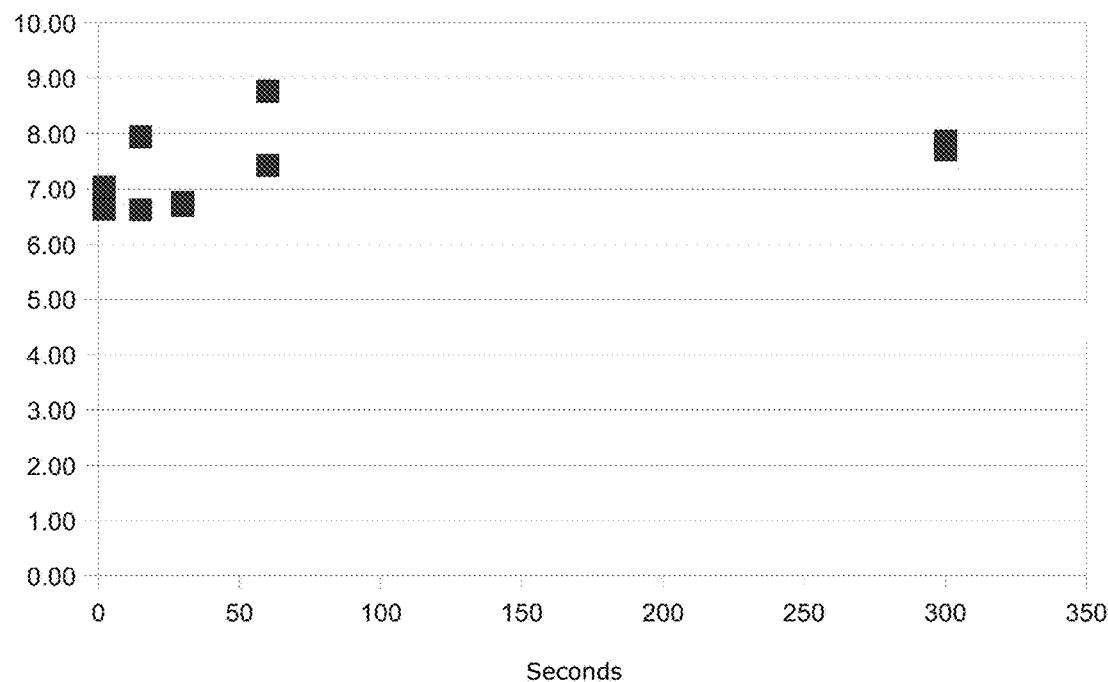
Figure 5D:
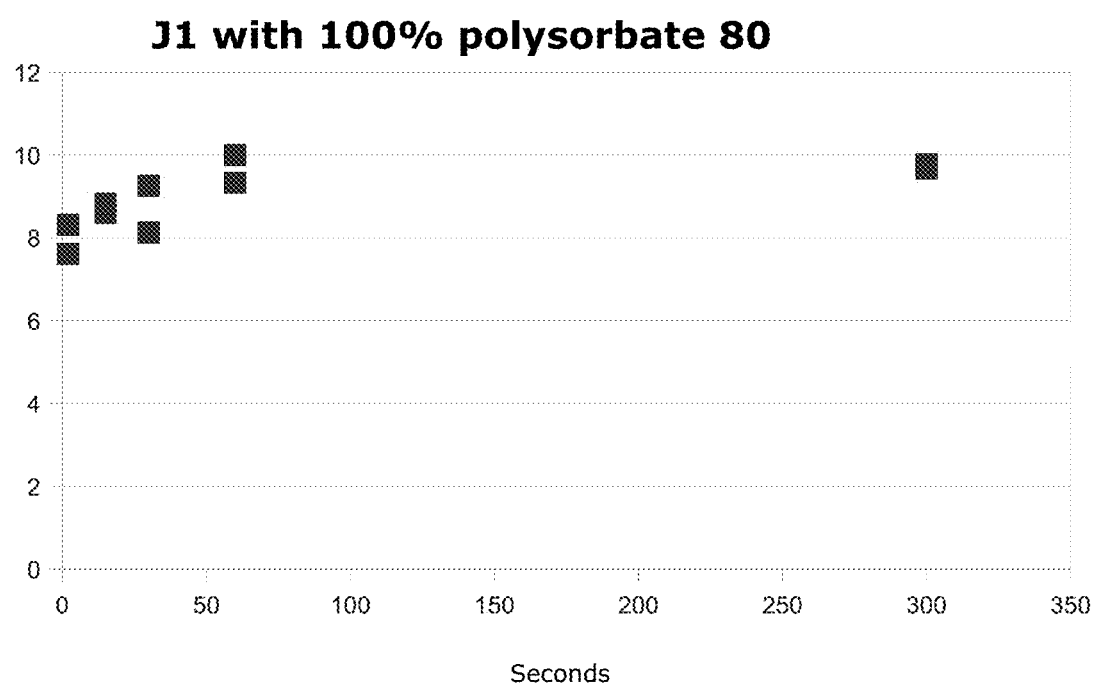

With this method the dissolution kinetics of freeze-dried J1 could be followed to complete dissolution after 3-4 min (see FIG. 3, no excipients and FIG. 4, with excipients, see also Table 8).

TABLE 8

Excipients additions to J1 (4 mg) on freeze-drying, Method B.

| Freeze dried material | Ratio J1:additive (mg J1:mg additive) | Number of experiments |
|---|---|---|
| J1:Mannitol | 4:20 | 1 |
| J1:Trehalose | 4:20 | 1 |
| J1:β-Cyclodextrin | 4:9 | 1 |
| J1-Polysorbate | 4:5 | 1 |
| J1:Trizma HCL | 4:8 | 1 |

The speed of dissolution of J1, with and without additives, determined with Method A and Method B, are summarized in Table 9.

TABLE 9

Summary of dissolution times of J1 with and without additives, Methods A and B.

| Freeze dried material | Ratio J1:additive (mg J1:mg additive) | Time (min) Method A | Time (min) Method B |
|---|---|---|---|
| J1 without additives | | <2 | 3-4 |
| J1:Trehalose | 4:2 | <2 | |
| J1:Trehalose | 4:10 | <2 | |
| J1:Trehalose | 4:20 | | 0.5-1 |
| J1:Sucrose | 4:10 | <2 | |
| J1:Mannitol | 4:2 | <2 | |
| J1:Mannitol | 4:10 | <2 | |
| J1:Mannitol | 4:20 | | 0.5-0.75 |
| J1:□ β-Cyclodextrin | 4:9 | <2 | 0.75-1 |
| J1:β-Cyclodextrin | 4:18 | <2 | |
| J1:Polysorbate | 4:0.05 | <2 | |
| J1:Polysorbate | 4:0.265 | <2 | |

TABLE 9-continued

Summary of dissolution times of J1 with and without additives, Methods A and B.

| Freeze dried material | Ratio J1:addative (mg J1:mg additive) | Time (min) Method A | Time (min) Method B |
|---|---|---|---|
| J1:Polysorbate | 4:5 | | 0.25-0.5 |
| J1:Trizma HCL | 4:8 | | >12 |

Purity and Recovery of J1

A sample of melphalan flufenamide hydrochloride (J1) was dissolved in 50% aq. acetonitrile and analyzed immediately with LCMS (Liquid chromatography-mass spectrometry), showing only one peak (>99%). The purity of J1 directly after dissolution in 70% ethanol containing 1 mM HCl or 5 mM HCl was found to be ca 97%, with a minor byproduct of ca 3%. The amount of this byproduct increased if the solution was left at room temperature.

The results demonstrate that the speed of dissolution of freeze-dried J1 in glucose solution with stirring was faster than could be measured (Method A), not enabling the effect of excipient additions to be seen. Using a more clinically relevant Method B without stirring, the dissolution of freeze-dried melphalan flufenamide in glucose solution could be followed to completeness after 3-4 minutes. Addition of excipients β-cyclodextrin, Polysorbate 80, Mannitol and Trehalose to the melphalan flufenamide solution before freeze-drying all gave complete dissolution below 1 minute. The fastest dissolution was given by Polysorbate 80 addition, giving complete dissolution at the first time-point 15 seconds.

Example 3: Test of Effect of Concentration of the Excipient Polysorbate 80 on the Dissolution Rate of Melphalan Flufenamide The following was performed to test the amount of the excipient Polysorbate 80 to be added in the freeze-drying process of melphalan flufenamide and to maximize the dissolution rate in a 5% glucose solution. 0, 10, 50 and 100% weight, in relation to melphalan flufenamide of Polysorbate 80 was used. The experiments were run in duplicate.

Melphalan flufenamide hydrochloride (J1) was used in all experiments. The Polysorbate 80 used was bought from Fluka, 59924-100 g.

Freeze-drying was done on a Leybold Lyovac GT2 equipment. LCMS was run on a HP1100-system using acetonitrile-0.1% trifluoroacetic acid in water as eluent. An ACE-column C8, 50×3 mm and a gradient 10-97% acetonitrile in 3 min was used. The filter vials were from Whatman, Mini-UniPrep, 0.45 μm.

General preparation of 2 mg/mL stock solution of melphalan flufenamide before freeze-drying was performed as follows:

11.0 mg melphalan flufenamide was suspended in 10 mM solution of HCl in absolute EtOH (0.5 mL). The mixture was stirred for 30 minutes before 0.2 mL water was added. The mixture was stirred for 10 minutes at room temperature (clear solution) before it was added to a 0° C. solution of water (4.8 mL). 0.25 mL of the solution was transferred to a plastic vial containing 10%, 50% or 100% weight Polysorbate 80. The vial was shaken, cooled and freeze-dried.

A 5% glucose solution with an internal standard 3-methoxybenzoic acid was prepared by dissolving 3-methoxybenzoic acid (1.2 mg) in water (15 mL). The mixture was stirred for 1 hour before 750 mg of glucose was added while stirring. 0.5 mL of the 5% glucose solution was added to each freeze-dried plastic vial and the mixtures were filtered, at different time-points, transferred to a glass vial and the dissolution of J1 was determined by HPLC.

Determination of Dissolution Rate

J1 (11 mg) was suspended in EtOH (0.5 mL) and stirred for 30 minutes at room temperature before water (5 mL) was added. The solution was divided into 4 different flasks containing 0%, 10%, 50% or 100% weight (in relation to J1) of Polysorbate 80. The solutions were transferred to 2 mL plastic vials and freeze-dried overnight.

A 5% glucose solution with an internal standard 3-methoxybenzoic acid was added to each vial without stirring and the mixtures were filtered through a 0.45 μm GHP vial insert at different time-points (2-300 seconds). The filtrate was immediately transferred to a glass vial to prevent leaking from undissolved material. The amount of dissolved J1 relative to the internal standard was determined using HPLC.

Results

The speed of dissolution of J1 (1 mg/mL in 5% glucose solution) with, and without Polysorbate 80, is summarized in Table 10 and depicture in FIG. 5.

TABLE 10

| Freeze-dried material (1 mg/mL) | Time to achieve steady state dissolution (seconds) |
|---|---|
| J1 without additive | 300-600 |
| J1 with 10% Polysorbate 80 | 30-60 |
| J1 with 50% Polysorbate 80 | 30-60 |
| J1 with 100% Polysorbate 80 | 30-60 |

Table 10 shows that all samples containing freeze-dried J1 and the excipient Polysorbate 80 dissolves much faster than J1 freeze-dried in the absence of excipient. Special attention was devoted to the sample containing 10% Polysorbate 80 and the time-points in this experiment were:

immediate filtration, 2 seconds, 15 seconds, 30 seconds and 5 minutes. In the first time-point where the sample was filtered immediately, approximately 40% was dissolved and after 2 seconds approximately 70% was dissolved. Full dissolution was achieved after 30-60 seconds.

The dissolution rate of freeze-dried J1 at 1 mg/mL containing varying amounts of Polysorbate 80 in a 5% glucose solution was under 1 minute for all samples. The lowest amount of Polysorbate 80 for rapid dissolution was between 10 and 50% by weight.

Example 4: Test of Effect of Concentrations of the Excipients Polysorbate 80, PEG 400 and β-Cyclodextrin on the Dissolution Rate of Melphalan Flufenamide This example was performed to study the effect of different concentrations of the excipients Polysorbate 80, PEG 400 and β-cyclodextrin added in the freeze-drying process of melphalan flufenamide to maximize the solubility and speed of dissolution in a 5% glucose solution towards the long-term goal of developing a lyophilized material, stable to storage and with facile preparation for dosing.

Melphalan flufenamide hydrochloride (J1) was used in all experiments.

Polysorbate 80 used was bought from Fluka (59924-100 g), β-cyclodextrin from Aldrich (856088) and PEG 400 from Clariant (100316).

Freeze-drying was done on a Leybold Lyovac GT2 equipment. LCMS was run on a HP1100-system using acetonitrile-0.1% trifluoroacetic acid in water as eluent. An ACE-column C8, 50×3 mm and a gradient 10-97% acetonitrile in 3 min was used. The filter vials were from Whatman, Mini-UniPrep, 0.45 μm.

General Preparation of 2 mg/mL Stock Solution of Melphalan Flufenamide for Freeze Drying 11.1 mg melphalan flufenamide was suspended in 10 mM solution of HCl in absolute EtOH (0.5 mL). The mixture was stirred for 30 minutes before 0.2 mL water was added. The mixture was stirred for 10 minutes at room temperature (clear solution) before it was added dropwise to a 0° C. solution of water (4.8 mL). 0.25 mL or 0.5 mL of the solution was transferred to a plastic vial containing the excipients. The vial was shaken, cooled and freeze-dried.

Solubility Experiment

A 5% glucose solution with an internal standard was prepared by dissolving 3-methoxybenzoic acid (1.2 mg) in water (15 mL). The mixture was stirred for 1 hour before 750 mg of glucose was added while stirring. 0.2 mL of the 5% glucose solution was added to each freeze-dried plastic vial and the mixtures were shaken for 10-15 seconds and filtered after 5 minutes. The filtrate was transferred to a glass vial and the solubility of melphalan flufenamide was determined by HPLC and a calibration curve.

Determination of Solubility

A 2 mg/mL stock solution of melphalan flufenamide hydrochloride (J1) was used as in previous experiments.

For a solubility of 2.5 mg/mL of J1 in 5% glucose solution, 0.25 mL of the stock solution was dispensed into 2 mL plastic vials containing a mixture of the excipients determined by experimental design and the mixtures were immediately cooled and freeze-dried.

The high/low levels of each excipient (in weight-% relative to melphalan flufenamide) were as follows: Polysorbate 80 (8%-80%), PEG 400 (80%-400%) and β-cyclodextrin (10%-50%). The highest amount of each excipient was determined from FDA Inactive Ingredient database of registered IV-administered drugs. β-cyclodextrin is on FDA's GRAS (Generally Recognized As Safe) list but no recommendations are given for intravenous injections to our knowledge, which caused a fairly conservative high level to be set. The weight percent of each excipient in relation to melphalan flufenamide hydrochloride (J1) (weight) is shown in Table 11.

TABLE 11

Weight percentage of each excipient in relation to J1.

| Experiment No | Polysorbate 80 [%] | PEG 400 [%] | β-cyclodextrin [%] |
|---|---|---|---|
| 1 | 8 | 400 | 10 |
| 2 | 8 | 80 | 10 |
| 3 | 8 | 400 | 50 |
| 4 | 8 | 80 | 50 |
| 5 | 80 | 400 | 10 |
| 6 | 80 | 80 | 10 |
| 7 | 80 | 400 | 50 |
| 8 | 80 | 80 | 50 |
| 9 | 44 | 240 | 30 |
| 10 | 44 | 240 | 30 |
| 11 | 44 | 240 | 30 |

As is demonstrated in other experiments herein, the dissolution rate of J1 increased markedly with the addition of Polysorbate 80 in the freeze drying process. Three experiments were performed to attempting to reach a solubility of 5 mg/mL. A stock solution of J1 was added to 3 different plastic vials (exp 12, 13 and 14) containing Polysorbate 80 (10%, 50% and 100% weight in relation to melphalan flufenamide). The mixtures were immediately cooled and freeze-dried.

A 5% glucose solution with an internal standard (3-methoxybenzoic acid) was added to each vial and the vials were shaken and allowed to stand for 5 minutes. The mixtures were filtered through a 0.45 μm GHP filter vial and the filtrate was immediately transferred to a glass vial to prevent leaking from undissolved material. The amount of dissolved J1 was determined using HPLC and a calibration curve.

Results

The solubilities of J1 in mg/mL with high/low levels of the excipients Polysorbate 80, PEG 400 and β-cyclodextrin are summarized in Table 12.

TABLE 12

Solubility of J1 in mg/mL.

| Experiment | Polysorbate 80 [%] | PEG 400 [%] | β-cyclodextrin [%] | Solubility of J1 [mg/ml] |
|---|---|---|---|---|
| 1 | 8 | 400 | 10 | 1.9 |
| 2 | 8 | 80 | 10 | 0.9 |
| 3 | 8 | 400 | 50 | 2 |
| 4 | 8 | 80 | 50 | 1.4 |
| 5 | 80 | 400 | 10 | 2 |
| 6 | 80 | 80 | 10 | 1.5 |
| 7 | 80 | 400 | 50 | 2 |
| 8 | 80 | 80 | 50 | 1.9 |
| 9 | 44 | 240 | 30 | 1.9 |
| 10 | 44 | 240 | 30 | 1.8 |
| 11 | 44 | 240 | 30 | 1.7 |
| 12 | 10 | x | x | 1 |
| 13 | 50 | x | x | 1.2 |
| 14 | 100 | x | x | 1.4 |
| 15* | x | x | x | 0.67 |
| 16* | x | x | x | 0.25 |
| 17 | 50 | 80 | 100 | 1.2 |

*Experiments 15-16 did not use freeze-dried J1, fine powder was used in Experiment 15 and larger lumps were used in Experiment 16.

The results provided in Table 12 demonstrates that the solubility of J1 increased in all experiments containing excipients compared to not freeze-dried J1 (entry 15 and 16).

The large discrepancy in the solubility of not freeze-dried J1 is probably due to different particle size in the batch, since entry 15 was a suspension of fine white powder, while entry 16 was larger lumps giving lower dissolution rate and hence lower solubility of J1 in 5 minutes. The precision of the analysis is shown in center experiments 9-11 (1.9, 1.8 and 1.7) with identical excipient concentrations. The 3 samples with Polysorbate 80 as the excipient (10, 50 and 100%) exhibited a solubility of 1.0, 1.2 and 1.4 mg/mL, respectively.

The entries with a mixture of the excipients Polysorbate 80, Peg 400 and β-cyclodextrin exhibited several combinations with solubilities at or close to 2.0 mg/mL. The highest determined solubilities 2.0 (entries 3, 5 and 7) were only attainable with high levels of PEG 400, giving liquids or semisolids after freeze drying.

The samples with lower amount of PEG 400 (entries 2, 4, 6 and 8) formed a white fluffy powder after freeze drying, with the highest determined solubility of 1.9 mg/mL in entry 8. This prompted testing if a higher solubility could be obtained by lowering the amount of PEG 400 and increasing the amount of β-cyclodextrin. An additional sample (row 17 in Table 12) was freeze-dried containing 50% Polysorbate 80, 80% of PEG 400 and 100% of β-cyclodextrin. The solubility of J1 with this mixture of excipients was 1.2 mg/mL.

The results demonstrate that the maximum solubility of J1 with combinations of excipients is close to 2 mg/mL.

With experiment 13 it was shown that a solution of J1 with 50% Polysorbate gave a solubility of approximately 1.2 mg/mL alone, sufficient for a 1.0 mg/mL formulation and allowing the exclusion of PEG 400 and β-cyclodextrin.

Visual Confirmation Experiments

To confirm the dissolution in a more clinically relevant setting, a larger scale experiment in transparent glass vials instead of plastic vials was performed. Vial 1 contained a solution 4.8 mg melphalan flufenamide hydrochloride (J1) and 2.4 mg Polysorbate 80. As a control vial 2 contained 4.8 mg melphalan flufenamide hydrochloride (J1) and no Polysorbate 80. The vials were freeze-dried overnight.

Figure 6:
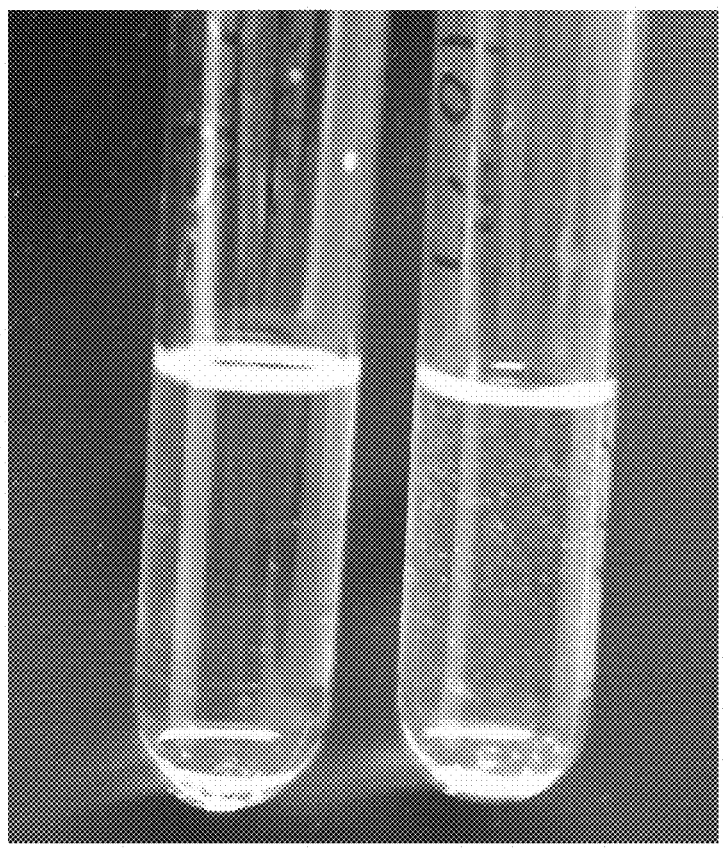
FIG. 6 is a photograph of glass tubes with melphalan flufenamide (J1) that following lyophilization is dissolved in a concentration of 1 mg/ml in a 5% glucose solution containing 50% (mol) Polysorbate 80 (left) and no Polysorbate 80 (right).

To each vial containing the freeze-dried melphalan J1 as white fluffy material, 4.70 mL of a 5% glucose solution was added to give a concentration of J1 of 1.02 mg/mL. The mixtures were shaken for 10-15 seconds and the test tube containing J1 and 50% Polysorbate 80 showed a clear solution after 15 seconds, see FIG. 6, left vial. The reference tube with freeze-dried J1 without the Polysorbate showed small particles and was not totally dissolved after 30 minutes, see FIG. 6, right vial. LC-MS analysis revealed that the purity of melphalan flufenamide after 30 minutes was >95%, in both vials.

The results provided herein demonstrate that the solubility of J1 in 5% glucose solution could be enhanced using a mixture of the excipients Polysorbate 80, Peg 400 and β-cyclodextrin to 1.9 mg/mL. Such a mixture of excipients with J1 resulted in a fluffy white solid on lyophilization.

Lyophilization of J1 with 50%-weight Polysorbate 80, resulted in a white fluffy solid that is rapidly dissolved in 5% glucose solution. The saturation concentration 1.2 mg/mL is sufficient to use in a clinical setting for dosing preparation at 1.0 mg/mL.

Example 5: Stability Test

The purpose of the first part of this study was to investigate the dissolution rate of melphalan flufenamide hydrochloride (J1) (freeze-dried together with Polysorbate 80) in 5% glucose solution.

The dissolution speed of J1 (freeze-dried) in 5% glucose solution containing Polysorbate 80 will be measured in another experiment.

Finally the dissolution speed of non-freeze dried J1 in 5% glucose solution containing Polysorbate 80 will be measured.

The second part is an investigation of the degradation of J1 in two different preparations at elevated temperature. The first preparation was a freeze dried solid containing polysorbate 80 and the second was a 25 mg/ml solution of J1 in N,N-dimethylacetamide (DMA). The degradation was followed for 1 month at +40° C., using two preparations (i) Determination of Dissolution Rate.

A 5% glucose solution was added to each plastic vial containing J1. The vials were were shaken and filtered at different time-points. The filtrate was transferred to glass vials and the amount of dissolved J1 was determined by HPLC.

(ii) Accelerated Stability Study Design.

Vials with freeze-dried J1 and Polysorbate 80, and 10 vials of J1 solution in DMA, were stored at 40° C. for 1 month. Two vials of the freeze-dried material (named freeze dried 1 and 2 in table below) and one vial of the DMA solution (named DMA in table 1 below) was taken out from the 40° C. chamber and stored at −20° C. and analysed at the same time for assay and purity of J1. Sample times were 0, 1, 3, 10 and 30 days. Each freeze dried vial contained 0.25 mg of J1. The 25 mg/ml solution in DMA was from Oncopeptides.

(iii) Analysis and Results

The freeze dried samples were dissolved in 500 μl DMA in Whatman 0.45 μm filter vials. The samples were vortexed briefly before pressing the two parts of the vial together and thus filtrating the sample. The 25 mg/ml solution samples were diluted with DMA by aliquoting 20 μl solution to HPLC vials and diluting with 980 μl DMA. 4 μl were injected in the chromatographic system.

The stability was evaluated as the relative purity, since there was a slight variation in the amount of J1 in the freeze dried vials. By using relative purity, each sample is standardised against itself and the effect of varying J1 amount is minimised on the stability result.

The speed of dissolution of J1 in 5% glucose in the presence of PS is summarized in table 13:

TABLE 13

Summary of dissolution experiments.

| | Time (min) to reach steady state dissolution | Content in plastic vial | Solution |
|---|---|---|---|
| Dissolution exp. 1 | 1 | freeze-dried J1 + Polysorbate 80 | 5% glucose |
| Dissolution exp. 2 | 1 | freeze-dried J1 | 5% glucose + Polysorbate 80 |
| Dissolution exp. 3 | 1-2 | non-freeze-dried J1 | 5% glucose + Polysorbate 80 |

Stability Test Results

TABLE 14

Results of stability test at 40° C., comparison between DMA solution and freeze-dried J1 at +40° C./Ambient Relative Humidity

| Day | Freeze dried 2 Relative [%] | Freeze dried 2 Relative [%] | Freeze dried Avg Relative [%] | DMA Relative [%] |
|---|---|---|---|---|
| 0 | 98.80 | 98.74 | 98.77 | 96.81 |
| 1 | 98.77 | 98.69 | 98.73 | 95.76 |
| 3 | 98.71 | 98.77 | 98.74 | 95.43 |
| 10 | 98.55 | 98.66 | 98.61 | 92.22 |
| 30 | 98.32 | 98.42 | 98.37 | 86.90 |

The results in table 14 show that the freeze dried material is essentially unchanged during the test period. Only a small change in purity can be observed. Also the dissolution rate of freeze-dried J1 at 1 mg/mL in a 5% glucose solution was under 1 min in the presence of Polysorbate 80. The dissolution rate of non-freeze-dried J1 at 1 mg/mL in a 5% glucose solution containing Polysorbate 80 was estimated to 1-2 min.

J1 in DMA solution degraded significantly during storage at +40° C. for one month. The relative amount decreased from about 96.8% to 86.9%. J1 stored as a freeze dried solid only showed a small degradation from 98.7% to 98.3% during the same period of time.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A lyophilized pharmaceutical preparation which is directly soluble in a physiologically acceptable aqueous solution, comprising melphalan flufenamide hydrochloride (J1) and sucrose.

2. The lyophilized pharmaceutical preparation according to claim 1, wherein the amount of sucrose is 10-100% by weight of said melphalan flufenamide hydrochloride (J1).

3. The lyophilized pharmaceutical preparation according to claim 1, which is free, or substantially free from organic solvents.

4. The lyophilized pharmaceutical preparation according to claim 2, which is free, or substantially free from organic solvents.

5. A pharmaceutical composition consisting of the lyophilized pharmaceutical preparation of claim 1 and a physiologically acceptable solution, wherein said physiologically acceptable solution is a glucose solution.

6. A pharmaceutical composition consisting of the lyophilized pharmaceutical preparation of claim 2 and a physiologically acceptable solution, wherein said physiologically acceptable solution is a glucose solution.

7. A pharmaceutical composition consisting of the lyophilized pharmaceutical preparation of claim 3 and a physiologically acceptable solution, wherein said physiologically acceptable solution is a glucose solution.

8. A pharmaceutical composition consisting of the lyophilized pharmaceutical preparation of claim 4 and a physiologically acceptable solution, wherein said physiologically acceptable solution is a glucose solution.

9. The lyophilized pharmaceutical preparation according to claim 1, in which sucrose is the sole excipient.

10. The lyophilized pharmaceutical preparation according to claim 9, which contains trace amounts of an organic solvent.

11. The lyophilized pharmaceutical preparation according to claim 1, which consists essentially of J1 and sucrose.

12. The lyophilized pharmaceutical preparation according to claim 11, which contains trace amounts of an organic solvent.

13. The lyophilized pharmaceutical preparation according to claim 9, which consists essentially of J1 and sucrose.

14. The lyophilized pharmaceutical preparation according to claim 13, which contains trace amounts of an organic solvent.

15. The lyophilized pharmaceutical preparation according to any one of claims 1 to 4, which is obtained by lyophilizing a solution comprising J1, sucrose, an organic solvent and water.

16. The lyophilized pharmaceutical preparation according to any one of claims 9 to 14, which is obtained by lyophilizing a solution of J1, sucrose, an organic solvent and water.

* * * * *